(12) United States Patent
Eidenschink et al.

(10) Patent No.: US 7,777,399 B2
(45) Date of Patent: Aug. 17, 2010

(54) MEDICAL BALLOON INCORPORATING ELECTROACTIVE POLYMER AND METHODS OF MAKING AND USING THE SAME

(75) Inventors: Tracee Eidenschink, Wayzata, MN (US); Derek Wise, New Brighton, MN (US); Derek Sutermeister, Eden Prairie, MN (US); Yousef Alkhatib, Maple Grove, MN (US); Daniel Gregorich, St. Louis Park, MN (US); Adam Jennings, Buffalo, MN (US); Matt Heidner, Maple Grove, MN (US); Dominick Godin, Mound, MN (US); Richard C. Gunderson, Maple Grove, MN (US); John Blix, Maple Grove, MN (US); Karl A. Jagger, Deephaven, MN (US); Angela Kornkven Volk, Rogers, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 434 days.

(21) Appl. No.: 11/496,248

(22) Filed: Jul. 31, 2006

(65) Prior Publication Data
US 2008/0086081 A1    Apr. 10, 2008

(51) Int. Cl.
*H01L 41/09* (2006.01)
*A61M 29/00* (2006.01)
(52) U.S. Cl. .............. 310/800; 604/96.01; 604/99.01
(58) Field of Classification Search ............ 310/800; 604/96.01, 99.01
See application file for complete search history.

(56) References Cited

U.S. PATENT DOCUMENTS

| | | | |
|---|---|---|---|
| 4,820,349 A | 4/1989 | Saab | 128/344 |
| 5,196,024 A | 3/1993 | Barath | 606/159 |
| 5,250,167 A | 10/1993 | Adolf et al. | 204/299 |
| 5,342,307 A * | 8/1994 | Euteneuer et al. | 604/103 |
| 5,573,520 A | 11/1996 | Schwartz et al. | 604/282 |
| 5,855,565 A | 1/1999 | Bar-Cohen et al. | 604/104 |
| 6,113,579 A | 9/2000 | Eidenschink et al. | 604/264 |
| 6,117,296 A | 9/2000 | Thomson | 204/607 |
| 6,123,718 A | 9/2000 | Tu et al. | 607/113 |
| 6,249,076 B1 | 6/2001 | Madden et al. | 310/363 |
| 6,388,043 B1 | 5/2002 | Langer et al. | 528/80 |

(Continued)

FOREIGN PATENT DOCUMENTS

WO        2006020457        2/2006

(Continued)

OTHER PUBLICATIONS

Croce, F.; Panero, S., Passerini, S., Scrosati, B., 39 *Electrochim. Acta* 255 (1994).

(Continued)

*Primary Examiner*—Thomas M Dougherty
(74) *Attorney, Agent, or Firm*—Vidas, Arrett & Steinkraus, P.A.

(57) ABSTRACT

An expandable medical balloon having at least one static state, at least one expanded state, and at least one deflated state, the expandable medical balloon including at least one active region, the at least one active region including electroactive polymer.

20 Claims, 57 Drawing Sheets

U.S. PATENT DOCUMENTS

| | | | |
|---|---|---|---|
| 6,514,228 B1 | 2/2003 | Hamilton et al. | 604/96.01 |
| 6,514,237 B1* | 2/2003 | Maseda | 604/533 |
| 6,517,515 B1 | 2/2003 | Eidenschink | 604/101.05 |
| 6,679,836 B2 | 1/2004 | Couvillon, Jr. | 600/146 |
| 6,749,556 B2 | 6/2004 | Banik | 600/30 |
| 6,770,027 B2 | 8/2004 | Banik et al. | 600/146 |
| 6,812,624 B1 | 11/2004 | Pei et al. | 310/800 |
| 6,835,173 B2 | 12/2004 | Couvillon, Jr. | 600/146 |
| 6,876,135 B2* | 4/2005 | Pelrine et al. | 310/339 |
| 6,921,360 B2 | 7/2005 | Banik | 600/30 |
| 6,940,211 B2 | 9/2005 | Pelrine et al. | 310/330 |
| 6,969,395 B2 | 11/2005 | Eskuri | 606/200 |
| 6,982,514 B1 | 1/2006 | Lu et al. | 310/300 |
| 6,991,639 B2* | 1/2006 | Holman et al. | 606/194 |
| 6,997,870 B2 | 2/2006 | Couvillon, Jr. | 600/146 |
| 7,077,808 B2 | 7/2006 | Couvillon, Jr. | 600/466 |
| 2003/0068522 A1 | 4/2003 | Wang | 428/654 |
| 2003/0236445 A1 | 12/2003 | Couvillon, Jr. | 600/114 |
| 2003/0236531 A1 | 12/2003 | Couvillon, Jr. | |
| 2004/0062930 A1 | 4/2004 | Roberts et al. | 428/411.1 |
| 2004/0068161 A1 | 4/2004 | Couvillon, Jr. | 600/143 |
| 2004/0087982 A1 | 5/2004 | Eskuri | 606/153 |
| 2004/0143160 A1 | 7/2004 | Couvillon, Jr. | 600/114 |
| 2005/0004425 A1 | 1/2005 | Banik | 600/30 |
| 2005/0037050 A1* | 2/2005 | Weber | 424/426 |
| 2005/0085693 A1 | 4/2005 | Belson et al. | 600/146 |
| 2005/0102017 A1 | 5/2005 | Mattison | 623/1.11 |
| 2005/0107669 A1 | 5/2005 | Couvillon, Jr. | 600/146 |
| 2005/0165439 A1* | 7/2005 | Weber et al. | 606/191 |
| 2005/0183259 A1 | 8/2005 | Eidenschink et al. | 29/508 |
| 2005/0228478 A1 | 10/2005 | Heidner | 623/1.11 |
| 2006/0041264 A1 | 2/2006 | Eskuri | 606/153 |
| 2006/0079836 A1 | 4/2006 | Holman et al. | |
| 2006/0111618 A1 | 5/2006 | Couvillon, Jr. | 600/152 |
| 2008/0249464 A1* | 10/2008 | Spencer et al. | 604/103 |
| 2009/0043254 A1* | 2/2009 | Pepper et al. | 604/103.07 |
| 2009/0054837 A1* | 2/2009 | Von Holst et al. | 604/103.08 |
| 2009/0054935 A1* | 2/2009 | Miller et al. | 606/86 R |
| 2009/0204082 A1* | 8/2009 | Wesselmann et al. | 604/264 |
| 2009/0227949 A1* | 9/2009 | Knapp et al. | 604/103.02 |
| 2009/0240105 A1* | 9/2009 | Smit et al. | 600/104 |
| 2009/0299327 A1* | 12/2009 | Tilson et al. | 604/500 |

FOREIGN PATENT DOCUMENTS

| | | |
|---|---|---|
| WO | 2007058691 | 5/2007 |

OTHER PUBLICATIONS

M. Yamaura et al., "Enhancement of Electrical Conductivity of Polypyrrole Film by Stretching: Counter-ion Effect", *Synthetic Metals*, vol. 36, (1988), pp. 209-224.

D. Zhou et al., "Actuators for the Cochlear Implant," *Synthetic Metals* 135-136 (2003) 39-40.

E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir*, 14 (11), 2970-2975, 1998.

E.W.H. Jager, E. Smela, O. Inganas, "Microfabricating Conjugated Polymer Actuators," *Science*, 290, 1540-1545, 2000.

E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999.

*Proceedings of the SPIE*, vol. 4329 (2001) entitled "Smart Structures and Materials" 2001. see Madden et al., "Polypyrrole actuators: modeling and performance," pp. 73-83.

Madden, John D. et al., "Fast Contracting Polypyrrole Actuators", *Synthetic Metals*, 113 (2000), pp. 185-192.

Madden, John D. et al., "Polypyrrole Actuatros: modeling and performance", *Proc. SPIE*, Vo. 4329 (2001) pp. 72-83.

http://www.azom.com... ElectroActive Polymers—EAPs pp. 1-7.

U.S. Appl. No. 11/280,120, filed Nov. 16, 2005, Weber et al.

U.S. Appl. No. 11/411,360, filed Apr. 25, 2006, Volk et al.

U.S. Appl. No. 11/368,927, filed Mar. 6, 2006, Volk et al.

U.S. Appl. No. 11/282,252, filed Nov. 18, 2005, Eidenschink et al.

\* cited by examiner

MEDICAL BALLOON INCORPORATING ELECTROACTIVE POLYMER AND METHODS OF MAKING AND USING THE SAME

FIELD OF THE INVENTION

The present invention relates to the field of medical balloons, in particular, medical balloons employing electroactive polymers.

BACKGROUND OF THE INVENTION

Balloon catheters, having expandable balloon members located at the distal end of the balloon catheter, are employed in a variety of medical procedures including as dilatation devices for compressing atherosclerotic plaque which results in a narrowing of the arterial lining, and for delivery and expansion of prosthetic devices such as stents, to a lesion site, i.e. vessel obstruction, within a body vessel.

One medical procedure where balloon catheters are employed is percutaneous transluminal coronary angioplasty (PTCA), or balloon angioplasty, which is a non-invasive, non-surgical means of treating peripheral and coronary arteries. This technique consists of inserting an uninflated balloon catheter into the affected artery. Dilation of the diseased segment of artery is accomplished by inflating the balloon which pushes the atherosclerotic lesion outward, thereby enlarging the arterial diameter.

In the most widely used form of angioplasty, a balloon catheter is guided through the vascular system until the balloon, which is carried at the distal end of a catheter shaft is positioned across the stenosis or lesion, i.e., vessel obstruction. The balloon is then inflated to apply pressure to the obstruction whereby the vessel is opened for improved flow.

In some embodiments, the catheter balloon may be utilized to expand and/or implant an expandable medical device such as a stent. When the balloon is expanded, the medical device or stent, which is situated on the balloon, is also expanded and released to aid in support and/or repair of the vessel wall.

Desirable characteristics for such assemblies include flexibility and maneuverability for ease of advancement through the body vessel, as well as thin walls and high strength. Another desirable characteristic due to the very small nature of these vessels is a low profile. It is also desirable to control dimensional changes in medical balloons including both radial and longitudinal expansion characteristics. Therefore, there has been a trend to downscale device sizes.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to strategic placement of electroactive polymer (EAP) on an expandable medical balloon to provide the balloon with active regions. Depending on the placement of EAP, a variety of balloon characteristics can be manipulated and/or improved.

In one aspect, the present invention relates to the strategic placement of EAP actuators on various components of a balloon catheter assembly.

In one aspect, the EAP actuators are employed on the inner and/or outer catheter shafts of a catheter assembly for controlling properties during delivery of the assembly through a patient's body lumen.

In one embodiment, EAP is disposed on the distal inner shaft of a catheter assembly to provide the distal inner shaft with a twisting function to aid in folding/rewrapping.

In one aspect, EAP active regions are strategically placed on the waists, cones or body of the balloon for selectively controlling expansion and deflation characteristics during use.

Furthermore, strategic placement on the inner and/or outer surface of the cones and/or balloon body can aid in stent securement, as well as withdrawal of the balloon after stent deployment by expansion and contraction of the EAP regions.

In one embodiment, the EAP active regions are employed for controlled expansion such that the balloon is expanded incrementally to the shape or curve of a body vessel.

In another embodiment, at least one EAP active region is disposed on the inner surface and/or outer surface of a selected region of the balloon such that at least one end region of the body can be expanded first, or on the inner and/or outer surface of the central region of a balloon body for center up deployment of an intraluminal medical device.

In one aspect, the EAP active regions are strategically placed on the balloon to improve folding and rewrapping characteristics. In one embodiment, the EAP active regions are disposed longitudinally on the balloon body to improve folding and rewrap. More specifically, in one embodiment, the EAP active regions are disposed on the balloon folds to achieve improved folding and rewrap. In another embodiment, the EAP active regions are disposed between the balloon folds to achieve improved folding and rewrap. Upon contraction of the EAP regions, the balloon can bend and fold upon itself.

The expandable balloon member can of course have EAP actuator disposed on the entirety of the surface. In some embodiments, the expandable balloon member is advantageously formed from EAP. This construction may be beneficial for applications where the balloon member is being employed for delivery of a secondary medical device such as a stent.

In another embodiment, a catheter assembly is provided with a sheath of EAP over the balloon for retaining the balloon in a folded configuration and for protection which is typically removed prior to the medical procedure. For SDS, the sheath is removed just prior to crimping the stent on the balloon.

In further embodiments, the EAP active regions may also be employed to modify or vary balloon properties such as the compliance characteristics of the balloon.

In another embodiment, the EAP active regions are employed to increase the surface lubricity of the device. When activated by application of voltage, the lubricious EAP extends out from the surface of the device providing a more slippery, lubricious surface.

In combination with any of the above embodiments, a lubricious coating may be employed.

In another embodiment, EAP is employed in combination with a lubricious coating. In one embodiment, an ionomeric gel is employed in combination with a lubricious coating.

The balloons according to the invention may be provided with other features including, but not limited to atherotomes or blades, markers for enhancing visibility, or other surface characteristics such as bumps, nodules, etc.

The atherotomes or blades may be formed from EAP, or otherwise provided with regions of EAP, for extending the blades up or outward radially, and for folding the blades down.

These and other aspects, embodiments and advantages of the present invention will be apparent to those of ordinary skill in the art upon review of the Detailed Description and Claims to follow.

DETAILED DESCRIPTION OF THE INVENTION

Figure 1:
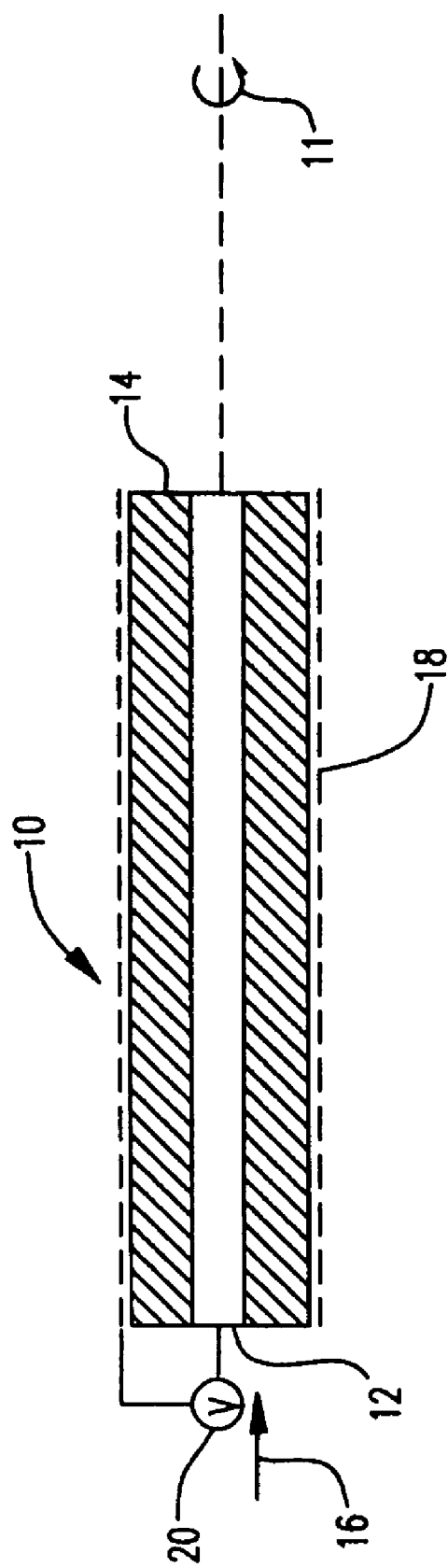
FIG. 1 is a schematic cross-sectional diagram of one embodiment of an electroactive polymer actuator useful in connection with the present invention.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

For the purposes of this disclosure, like reference numerals in the figures shall refer to like features unless otherwise indicated.

Depicted in the figures are various aspects of the invention. Elements depicted in one figure may be combined with, or substituted for, elements depicted in another figure as desired.

The expandable medical balloons according to the invention may be actuated, at least in part, with electroactive polymer (EAP) actuators. Electroactive polymers are characterized by their ability to change shape in response to electrical stimulation. EAPs can be divided into two categories including electronic EAPs (driven by an electric field) and ionic EAPs (involving mobility or diffusion of ions).

Electronic EAPs (electrorestrictive, electrostatic, piezoelectric, ferroelectric) can be induced to change their dimensions by applied electric fields. Examples of materials in this category include ferroelectric polymers (commonly known polyvinylidene fluoride and nylon 11, for example), dielectric EAPs, electrorestrictive polymers such as the electrorestrictive graft elastomers and electro-viscoelastic elastomers, and liquid crystal elastomer composite materials wherein conductive polymers are distributed within their network structure.

Ionic EAPs are typically employed in connection with the present invention. Ionic EAPs include ionic polymer gels, ionomeric polymer-metal composites, conductive polymers and carbon nanotubes.

The induced displacement of both electronic EAPs and ionic EAPs can be geometrically designed to bend, stretch or contract.

Common polymer materials such as polyethylene, polystyrene, polypropylene, etc., can be made conductive through compounding techniques involving the addition of conductive fillers which impart their conductive properties to the polymer by forming conductive current-carrying paths through the polymer matrix. The polymer matrix is insulative, but the composite exhibits conductive properties via the filler. These polymers are almost exclusively thermoplastic, but thermosetting materials such as epoxies, may also be employed. Suitable conductive fillers include metals and carbon (usually carbon black or fiber). These can be in the form of sputter coatings or other means can be employed through which a pattern of conductive material can be applied.

Ionic polymer gels are activated by chemical reactions and can become swollen upon a change from an acid to an alkaline environment.

Ionomeric polymer-metal composites can bend as a result of the mobility of cations in the polymer network. Suitable base polymers include perfluorosulfonate and perfluorocarboxylate.

Essentially any electroactive polymer that exhibits contractile or expansile properties may be used in connection with the various active regions of the invention, including any of those listed above.

In some embodiments herein, the ionic EAPs are conductive polymers that feature a conjugated backbone (they include a backbone that has an alternating series of single and double carbon-carbon bonds, and sometimes carbon-nitrogen bonds, i.e. π-conjugation) and have the ability to increase the electrical conductivity under oxidation or reduction. These polymers allow freedom of movement of electrons, therefore allowing the polymers to become conductive. The pi-conjugated polymers are converted into electrically conducting materials by oxidation (p-doping) or reduction (n-doping).

CPs actuate via the reversible counter-ion insertion and expulsion that occurs during redox cycling. Dimensional or volumetric changes can be effectuated via mass transfer of ions into or out of the polymer. This ion transfer is used to build the conductive polymer actuators. The EAP-containing active region contracts and/or expands in response to the flow of ions out of, or into, the same. For example, in some conductive polymers, expansion is believed to be due to ion insertion between chains, whereas in others inter-chain repulsion is believed to be the dominant effect. Regardless of the mechanism, the mass transfer of ions into and out of the material leads to an expansion or contraction of the polymer, delivering significant stresses (e.g., on the order of 1 MPa) and strains (e.g., on the order of 10%). These characteristics are ideal for construction of the devices of the present invention. As used herein, the expansion or the contraction of the active region of the device is generally referred to as "actuation." These exchanges occur with small applied voltages and voltage variation can be used to control actuation speeds.

Upon application of a small voltage, as small as 1 or 2 volts, and proper design of a substrate, ionic EAPs can bend significantly. Ionic EAPs also have a number of additional properties that make them attractive for use in the devices of the present invention, including the following: (a) lightweight, flexible, small and easily manufactured; (b) energy sources are available which are easy to control, and energy can be easily delivered to the EAPS; (c) small changes in potential (e.g., potential changes on the order of 1V; d) can be used to effect volume change in the EAPs; (e) relatively fast in actuation (e.g., full expansion/contraction in a few seconds); (f) EAP regions can be created using a variety of techniques, for example, electrodeposition; and (g) EAP regions can be patterned, for example, using photolithography, if desired.

Some commonly known conductive EAPS include, but are not limited to, polypyrroles, polyanilines, polythiophenes, polyethylenedioxythiophenes, poly(p-phenylenes), poly(p-phenylene vinylene)s, polysulfones, polypyridines, polyquinoxalines, polyacetylenes, polyanthraqinones, poly(n-vinylcarbazole)s, etc., with the most common being polythiophenes, polyanilines, and polypyrroles.

Some of the structures are shown below:

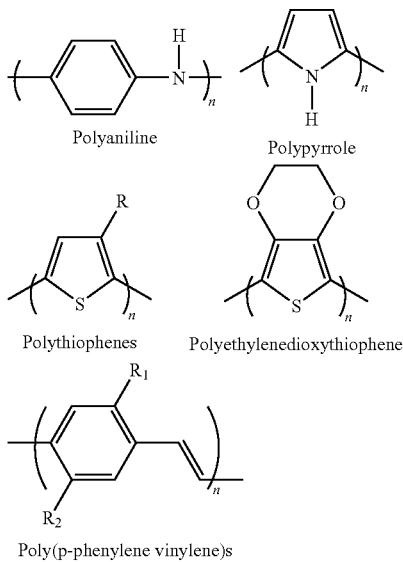

Polyaniline    Polypyrrole

Polythiophenes    Polyethylenedioxythiophene

Poly(p-phenylene vinylene)s

Polypyrrole, shown in more detail below, is one of the most stable of these polymers under physiological conditions:

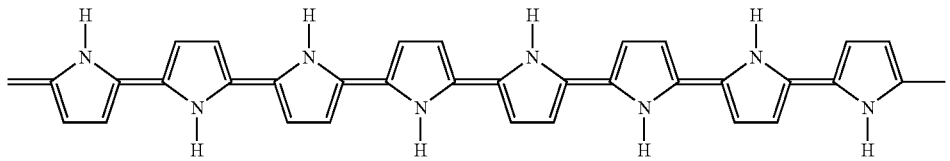

The above list is intended for illustrative purposes only, and not as a limitation on the scope of the present invention.

Additionally, the following elements are commonly utilized to bring about electroactive polymer (EAP) actuation: (a) a source of electrical potential, (b) an active region, which comprises the electroactive polymer, (c) a counter electrode and (d) an electrolyte in contact with both the active region and the counter electrode.

Referring now the drawings, FIG. 1 is a schematic cross-sectional diagram of an electroactive polymer (EAP) actuator 10 useful in connection with the present invention illustrating each of the elements commonly utilized in inducing EAP actuation. This diagram is reproduced from commonly assigned U.S. Pat. No. 6,679,836, the entire content of which is incorporated by reference herein.

Active region 12 of actuator 10 has a surface coupled with electrolyte 14 and has an axis 11. Active region 12 includes an electroactive polymer that contracts or expands in response to the flow of ions out of, or into, the active region 12. Ions are provided by electrolyte 14, which adjoins region 12 over at least a portion, and up to the entirety, of the surface of active region 12 in order to allow for the flow of ions between the two media. Many geometries are available for the relative disposition of active region 12 and electrolyte 14.

For example, active region 12 may be a film, fiber or group of fibers, combination of multiple films and fibers, etc. The fibers may be bundled or distributed within the electrolyte 14. These are, however, examples of distributions intended for illustrative purposes only, and not to limit the scope of the present invention.

Active region 12 includes at least one EAP. Any suitable polymer which exhibits contractile or expansile properties with the right elements and actuator construction may be employed herein as discussed above.

As an example, active region 12 may include polypyrroles, polyanilines, polythiophenes, polyethylenedioxythiophenes, poly(p-phenylenes), poly(p-phenylene vinylene)s, polysulfones, polypyridines, polyquinoxalines, polyacetylenes, polyanthraqinones, poly(n-vinylcarbazole)s, etc., with polypyrroles, being a particularly suitable polymer due to biocompatibility.

Ionic EAPs, driven by diffusion of ions, suitably include at least one electrolyte 14 for the actuation mechanism. The electrolyte 14, which is in contact with at least one portion of the surface of the active region 12, allows for the flow of ions and thus acts as a source/sink for the ions. The electrolyte 14 may be, for example, solid, liquid or gel, providing that ion movement is permitted. Where the electrolyte 14 is a solid, it should move with the active member 12 and should not be subject to delamination. Suitably, the electrolyte is preferably non-toxic in the event that a leak inadvertently occurs in vivo.

A liquid electrolyte, may be for example, an aqueous solution including at least one salt, such as a solution of NaCl, sodium dodecylbenzene sulfonate, phosphate, buffered solution, physiological solutions, or some appropriate mixture thereof. Gels include, for example, a salt doped agar gel or polymethylmethacrylate (PMMA) gel containing a salt dopant. Solid electrolytes include ionic polymers different from the EAP and salt films. Solid electrolytes include polymer electrolytes, for example, perfluorocarbon materials such as NAFION® perfluorosulfonic acid polymer available from DuPont de Nemours & Company. Solid electrolytes have also been prepared using propylene carbonate, ethylene carbonate, polyacrylonitrile and cupric perchlorate, for example. See Croce, F.; Panero, S., Passerini, S., Scrosati, B., 39 *Electrochim. Acta* 255 (1994).

The electrolyte, which is in contact with at least a portion of the surface of the active region, allows for the flow of ions and thus acts as a source/sink for the ions. Any suitable electrolyte may be employed herein.

Counter electrode 18 is in electrical contact with electrolyte 14 in order to provide a return path for charge to a source 20 of potential difference between member 12 and electrolyte 14. The counter electrode 18 may be formed using any suitable electrical conductor, for example, another conducting polymer, a conducting polymer gel, or a metal, such as stainless steel, gold, platinum, copper, etc. At least a portion of the surface of the counter electrode 18 is in contact with the electrolyte 14, in order to provide a return path for charge.

Counter electrode 18 may be in the form of a wire, such as a wire winding, or may be applied by any suitable means including electroplating, chemical deposition, or printing. In order to activate actuator 10, a current is passed between active member 12 and counter electrode 18, inducing contraction or expansion of member 12.

The source of electrical potential for use in connection with the present invention can be quite simple, consisting, for example, of a dc battery and an on/off switch. Alternatively, more complex systems can be utilized. For example, an electrical link can be established with a microprocessor, allowing a complex set of control signals to be sent to the EAP-containing active region(s).

Additionally, the behavior of conducting polymers such as the conjugated polymers described herein can be dramatically altered with the addition of charge transfer agents (dopants). Various dopants can be used in the polypyrrole-containing active regions, including large immobile anions (p-doping) and large immobile cations (n-doping). These materials can be oxidized to a p-type doped material by doping with an anionic dopant species or reducible to a n-type doped material by doping with a cationic dopant species. Generally, polymers such as polypyrrole (PPy) are partially oxidized to produce p-doped materials:

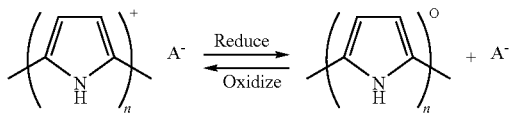

Dopants have an effect on this oxidation-reduction scenario and convert semi-conducting polymers to conducting versions close to metallic conductivity in many instances. Such oxidation and reduction are believed to lead to a charge imbalance that, in turn, results in a flow of ions into or out of the material. These ions typically enter/exit the material from/into an ionically conductive electrolyte medium associated with the electroactive polymer.

In a specific embodiment, polypyrrole-containing active regions may fabricated using a number of known techniques, for example, extrusion, casting, dip coating, spin coating, or electro-polymerization/deposition techniques. Such active regions can also be patterned, for example, using lithographic techniques, if desired.

As a specific example, polypyrrole films may be synthesized by electrodeposition according to the method described by M. Yamaura et al., "Enhancement of Electrical Conductivity of Polypyrrole Film by Stretching: Counter-ion Effect," *Synthetic Metals*, vol. 36, pp. 209-224 (1988), which is incorporated herein by reference.

As another specific example of a fabrication technique, polypyrrole can be galvanostatically deposited on a platinised substrate from a pyrrole monomer solution using the procedures described in D. Zhou et al., "Actuators for the Cochlear Implant," *Synthetic* Metals 135-136 (2003) 39-40, the content of which is incorporated by reference herein. Polypyrrole can also be deposited on gold. In some embodiments, adhesion of the electrodeposited polypyrrole layer is enhanced by covering a metal such as gold with a chemisorbed layer of molecules that can be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

According to one specific embodiment, the active region comprises polypyrrole (PPy) doped with dodecylbenzene sulfonate (DBS) anions. When placed in contact with an electrolyte containing small mobile cations, for example, $Na^+$ cations, and when a current is passed between the polypyrrole-containing active region and a counter electrode, the cations are inserted/removed upon reduction/oxidation of the polymer, leading to expansion/contraction of the same. This process can be represented by the following equation:

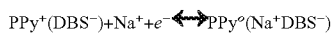

where $Na^+$ represents a sodium ion, $e^-$ represents an electron, $PPy^+$ represents the oxidized state of the polypyrrole, $PPy^o$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups, available from E.I. DuPont Co., Inc. of Wilmington, Del.

Electroactive polymers are also discussed in detail in commonly assigned copending U.S. Patent Publication No. 2005/0165439, the entire content of which is incorporated by reference herein.

The actuators according to the invention can be provided in an essentially infinite array of configurations as desired, including planar actuator configurations (e.g., with planar active members and counter-electrodes), cylindrical actuator configurations (e.g., see the actuator illustrated in FIG. 1), and so forth.

EAP-containing active regions can be provided that expand and contract when an applied voltage of appropriate value is interrupted depending, for example, upon the selection of the EAP, dopant, and electrolyte. This can include dimensional changes in length, width, depth or combination thereof depending on the composition and configuration of the EAP actuator and how it may be disposed on a substrate, for example.

As part of a failsafe mechanism for the devices of the present invention, it may be beneficial to select actuators that are of a type that relax in the event that power is interrupted.

Additional information regarding EAP actuators, their design considerations, and the materials and components that may be employed therein, can be found, for example, in E. W. H. Jager, E. Smela, O. Inganäs, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems*, 8(4), 373-383, 1999; U.S. Pat. No. 6,249,076, assigned to Massachusetts Institute of Technology, and *Proceedings of the SPIE*, Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

In certain other embodiments, the medical devices of the present invention are actuated, at least in part, using materials involving piezoelectric, electrostrictive, and/or Maxwell stresses.

Figure 2A:
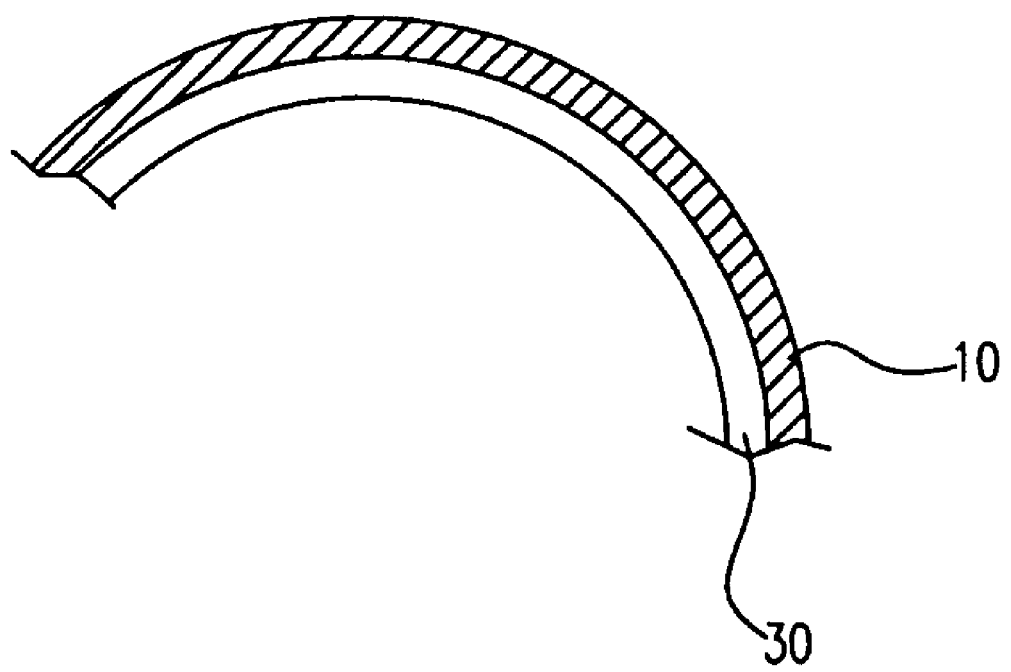
FIG. 2A is a cross-sectional view of a substrate having an EAP actuator 10 of a type which can be similar to that shown in FIG. 1 disposed thereon after EAP has been actuated.

FIG. 2A is a cross-sectional view of a substrate 30 having an EAP actuator 10 of a type which can be similar to that shown in FIG. 1 disposed thereon. EAP actuator 10 is configured to lengthen upon application of an applied voltage.

Figure 2B:
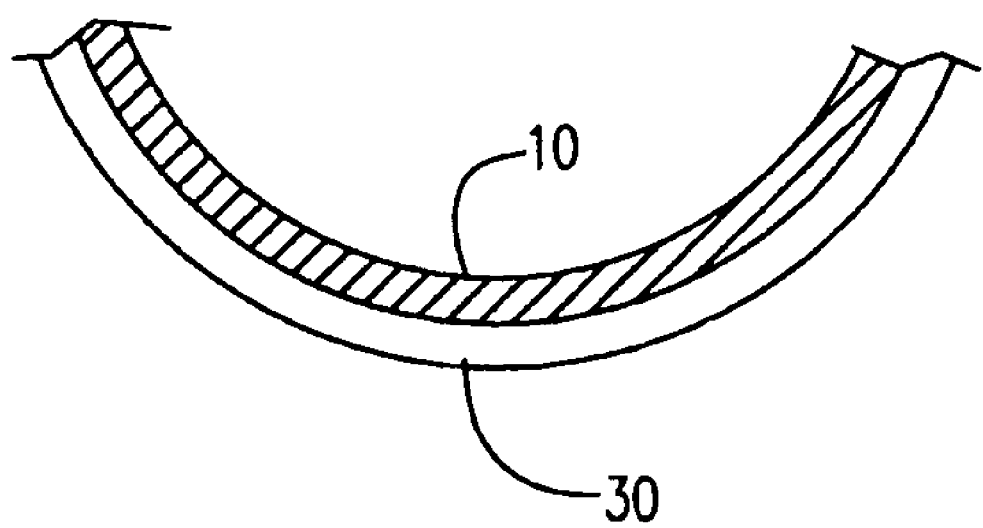
FIG. 2B is a cross-sectional view of a substrate having an EAP actuator of a type which can be similar to that shown in FIG. 1 disposed thereon after EAP has been actuated.

Alternatively, FIG. 2B is a cross-sectional view of a substrate 30 having EAP actuator 10 of a type which can be similar to that shown in FIG. 1 disposed thereon. EAP actuator 10 is configured to shorten upon application of an applied voltage.

Figure 3A:
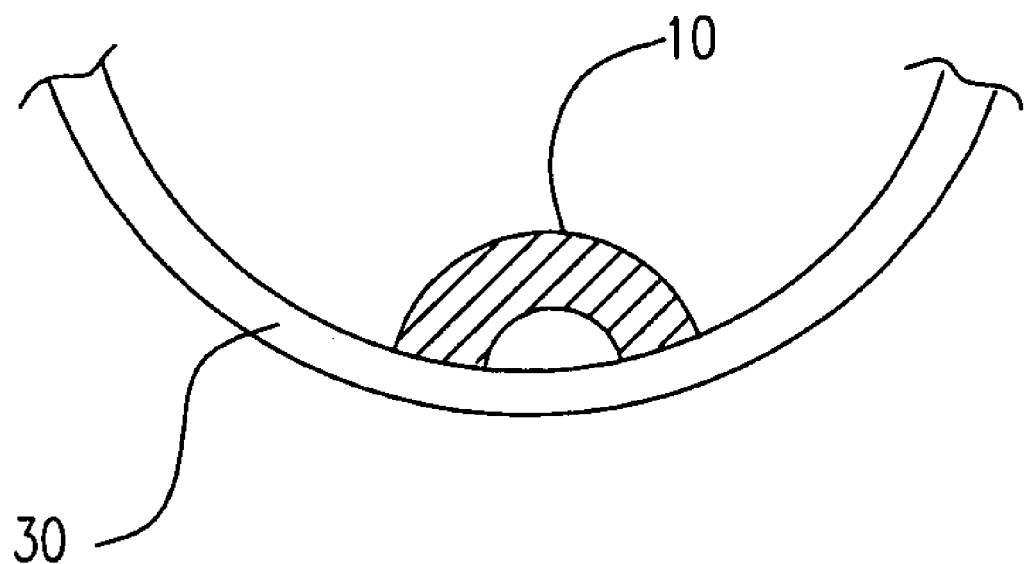
FIGS. 3A and 3B are cross-section views of a substrate having an EAP actuator disposed thereon before and after actuation of the EAP actuator respectively.
Figure 3B:
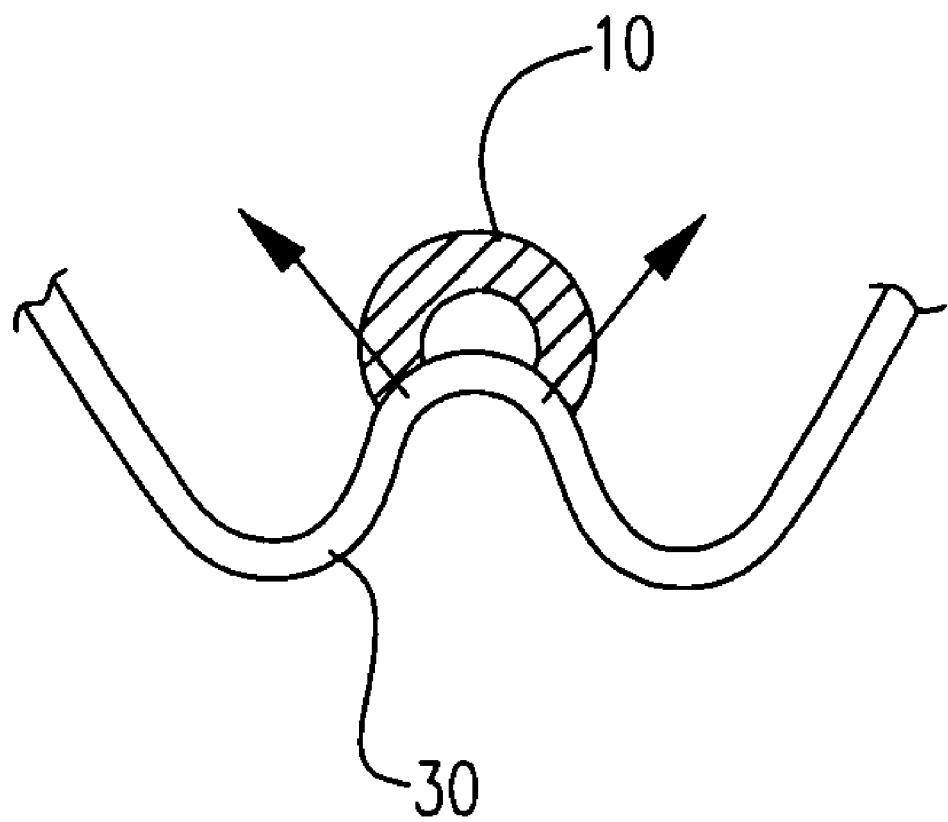

FIGS. 3A and 3B are cross-sectional views of a substrate 30 having an EAP actuator 10 mounted thereon. FIG. 3B is a cross-sectional view of the substrate 30 after actuation of the EAP actuator 10.

The EAP actuator 10 may be configured in other arrays, for example, actuator 10 may include an active region 12 and counter electrode 18 with an intervening electrolyte 14. See U.S. Pat. No. 6,679,836, the entire content of which is incorporated by reference herein.

Figure 4:
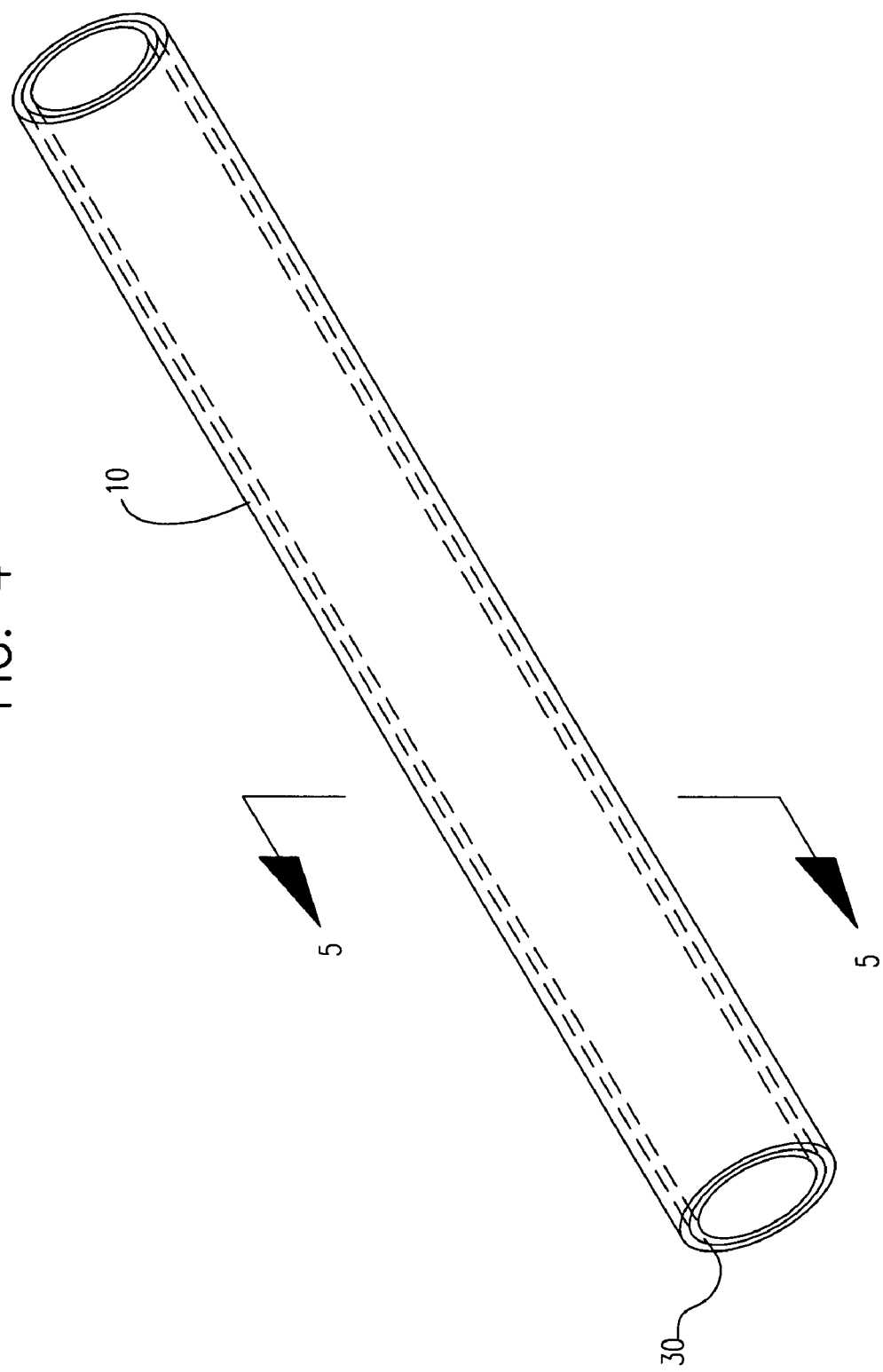
FIG. 4 is a perspective view of a tubular member having an EAP actuator of a type which may be similar to that shown in FIG. 1 disposed thereon.
Figure 5:
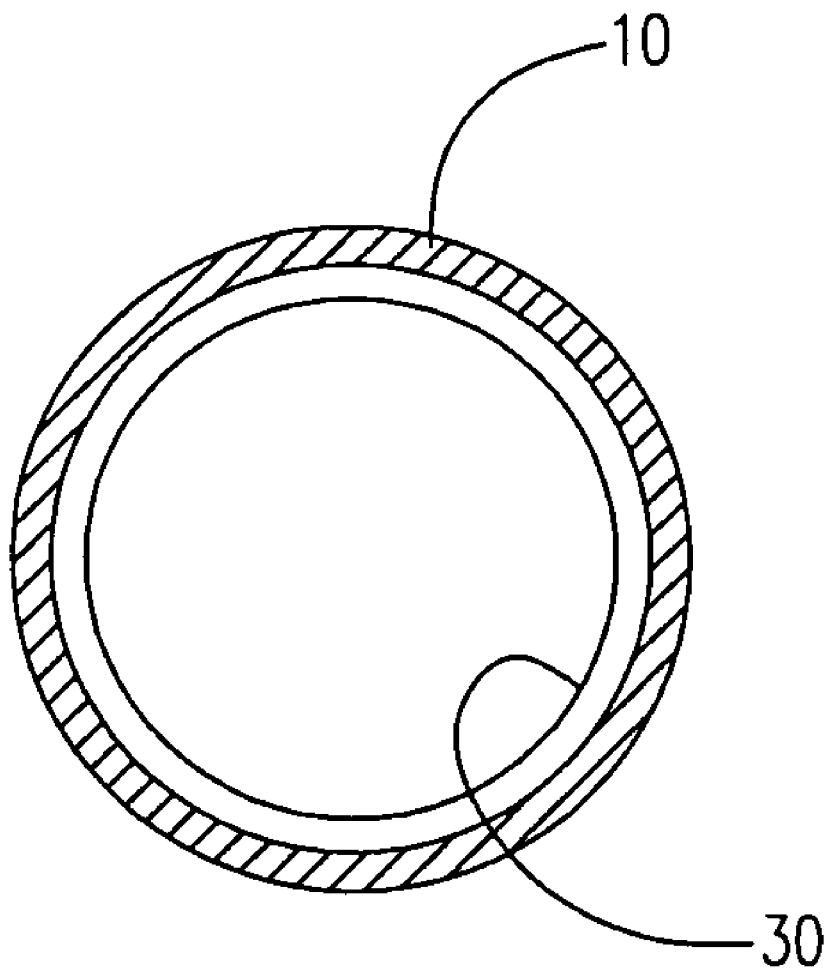
FIG. 5 is a cross-sectional view taken at section 5-5 in FIG. 4.

FIG. 4 is a perspective view of a tubular member 30 having an EAP actuator 10 disposed thereon. EAP actuator 10 may be of the type described in FIG. 1, or may have a different configuration as discussed in the paragraph above. This tubular structure is shown prior to activation of EAP actuator 10. A cross-sectional view, shown in FIG. 5, is taken at section 5-5 in FIG. 4.

Figure 6:
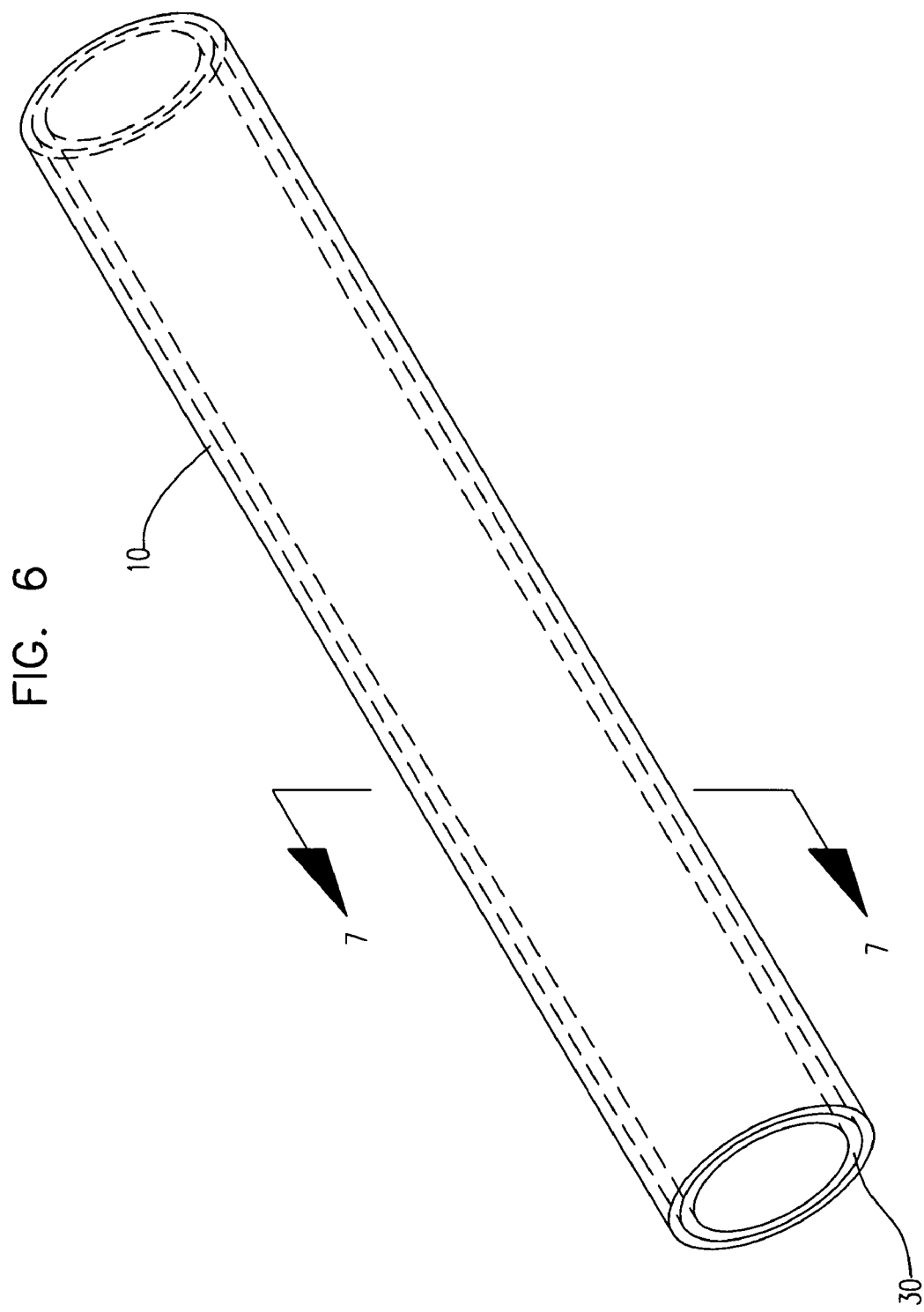
FIG. 6 is a perspective view of a tubular member having an EAP actuator of a type which may be similar to that shown in FIG. 1 disposed thereon after actuation of EAP.
Figure 7:
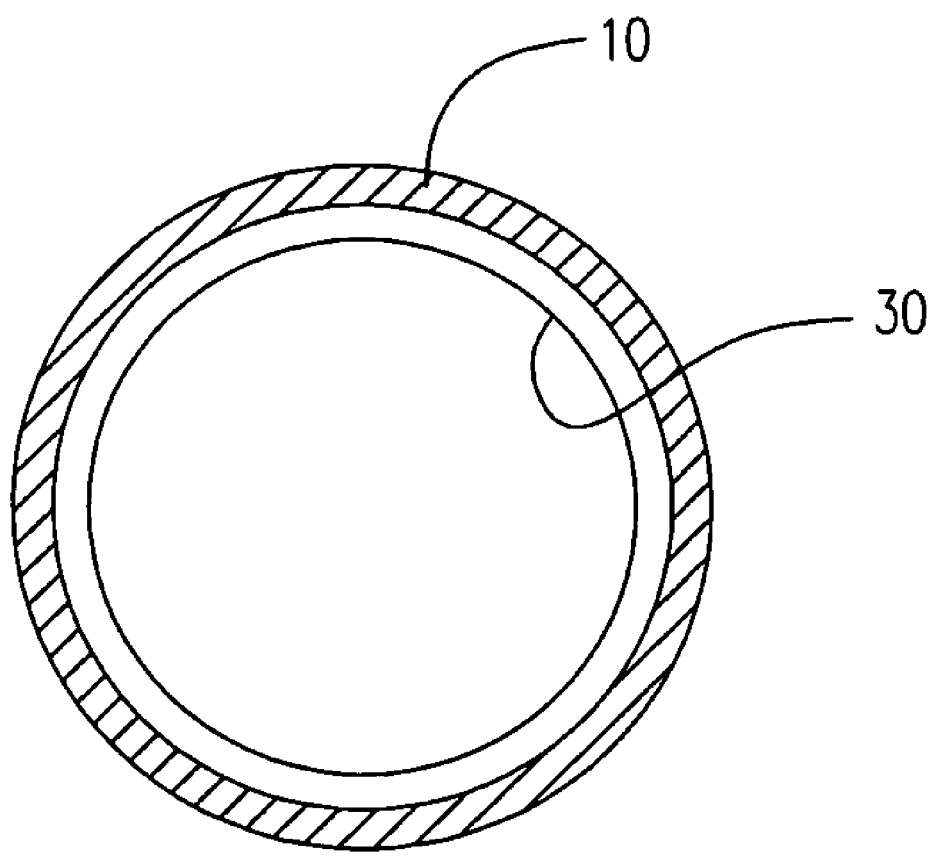
FIG. 7 is a cross-sectional view taken at section 7-7 in FIG. 6.

FIG. 6 is a perspective view illustrating a tubular member similar to that shown in FIG. 4 after actuation of EAP actuator 10. EAP polymer has expanded in this case, causing the entire tubular member to expand. A cross-sectional view, shown in FIG. 7, is taken at section 7-7 in FIG. 6.

Figure 8:
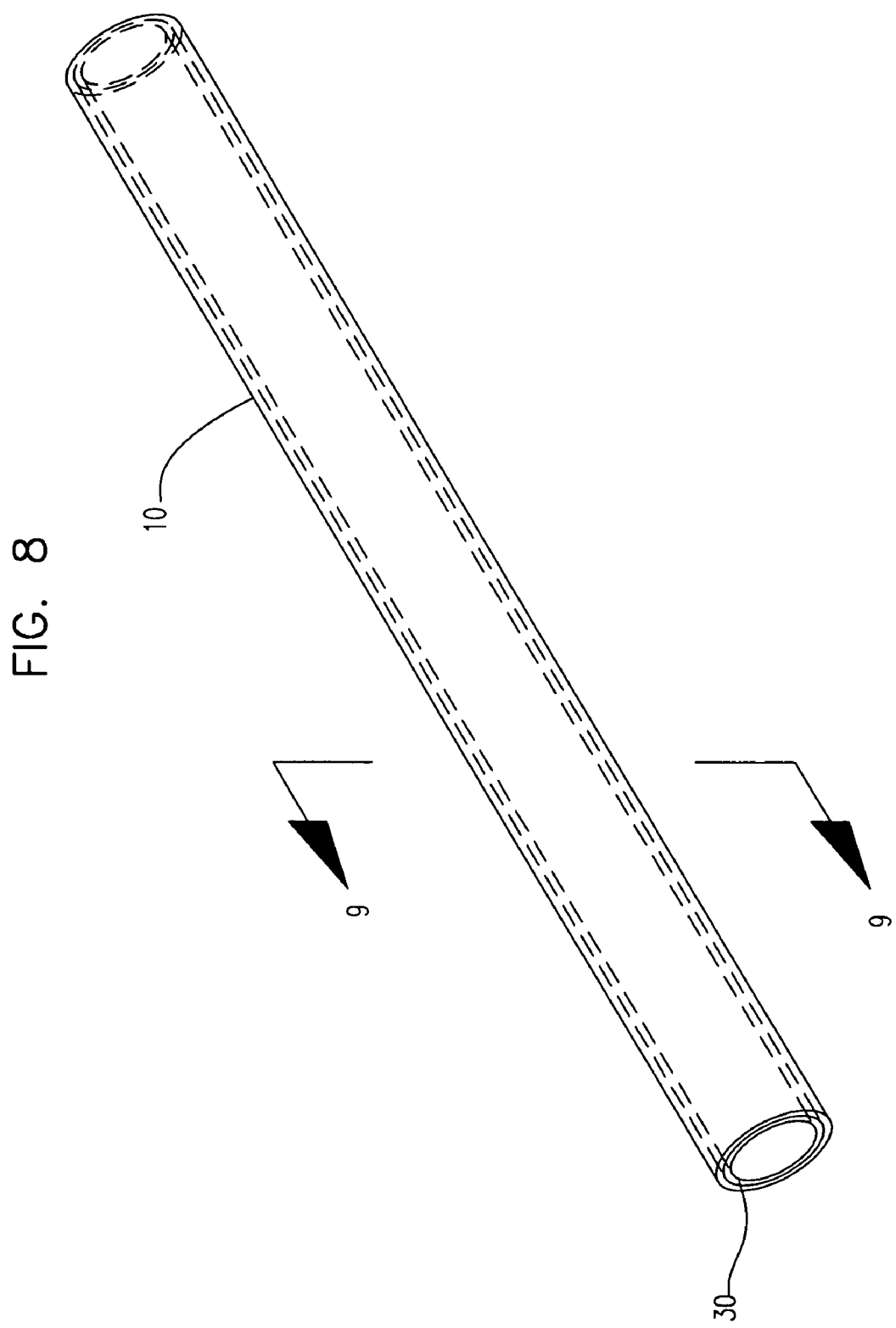
FIG. 8 is a perspective view of a tubular member having an EAP actuator of a type which may be similar to that shown in FIG. 1 disposed thereon after actuation of EAP.
Figure 9:
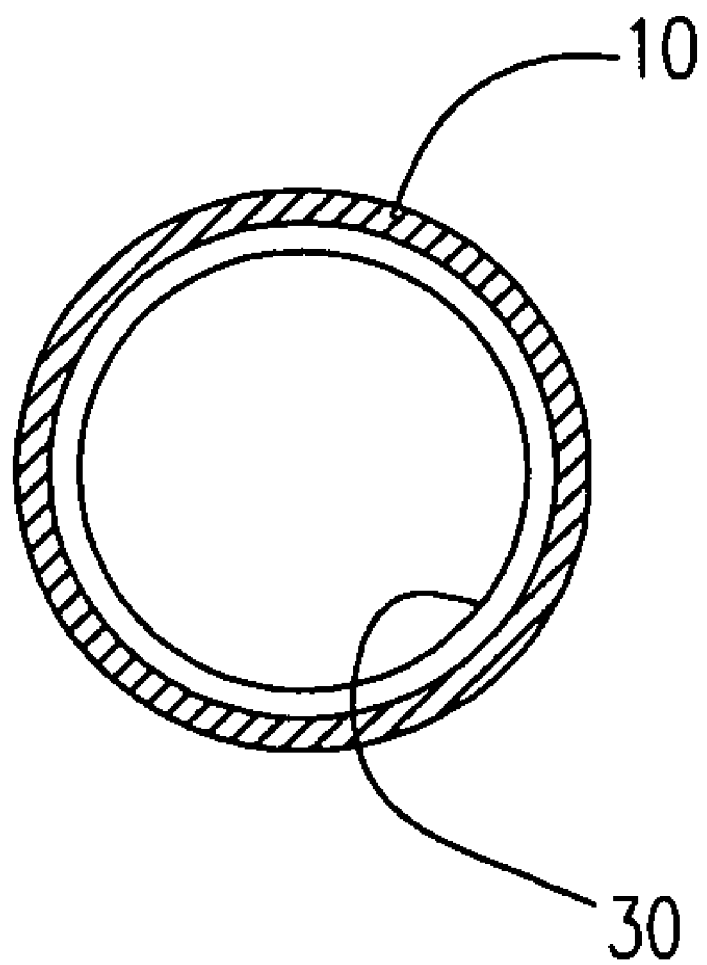
FIG. 9 is a cross-sectional view taken at section 9-9 in FIG. 6. is a perspective view of a balloon having an EAP region according to the invention.

Alternatively, FIG. 8 is a perspective view of a tubular member similar to that shown in FIG. 4, after actuation of EAP actuator 10, resulting in contraction of the EAP polymer and corresponding decrease in dimension of the entire tubular structure. FIG. 9 is a cross-sectional view of the tubular structure taken at section 9-9 in FIG. 8.

These concepts according to the present invention, find utility in the construction and use of balloon catheters, and the expandable balloon members which are employed thereon as can be seen from the discussion below. For example, EAP active region(s) 10 may be placed on inner and/or outer surfaces of catheter shafts, on the inner and/or outer surface of the balloon cones, circumferentially on the inner and/or outer surface of the balloon body, longitudinally on the inner and/or outer surface of the balloon body, or on inner and/or outer sides of balloon folds, or any combination thereof. The following figures represent various aspects of this strategic placement.

Figure 10:
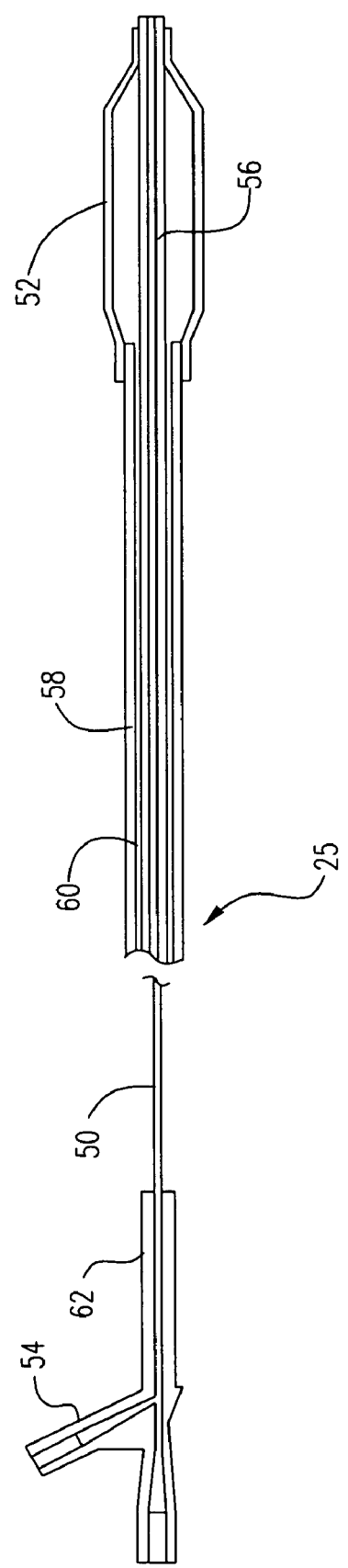
FIG. 10 is a longitudinal cross-sectional view of one embodiment of a balloon catheter assembly.

FIG. 10 is a longitudinal cross-sectional view illustrating an embodiment of a balloon catheter assembly 25. Balloon catheter assembly 25 may be modified using EAP actuators as will be described. FIG. 10 illustrates a representative OTW angioplasty balloon catheter according to the invention. Such balloon catheters are discussed, for example, in commonly assigned U.S. Pat. Nos. 6,113,579, 6,517,515, 6,514,228, each of which is incorporated by reference herein in its entirety. In this embodiment, catheter 25 has an elongate shaft assembly 50 and an expandable balloon member 52. A conventional OTW-type manifold assembly 54 shown with a strain relief 62 is connected to proximal end of shaft assembly 50. The shaft assembly 50 includes an inner tube 56 and an outer tube 58. Outer tube 58 is coaxially disposed about inner tube 56 to define an annular inflation lumen 60.

Figure 11A:
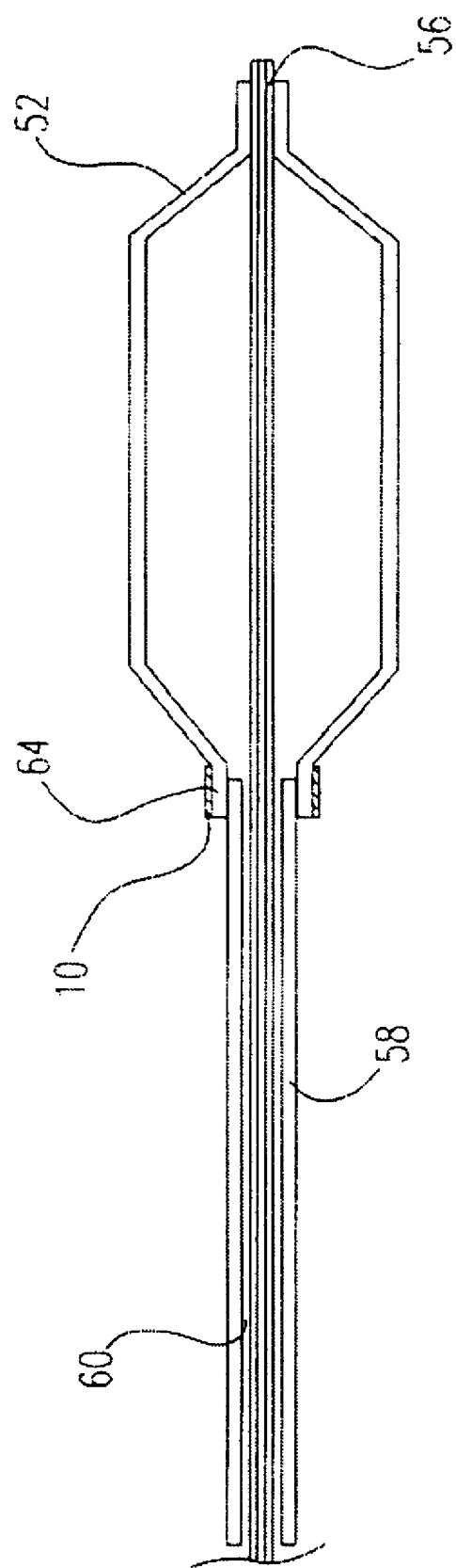
FIG. 11a is a longitudinal cross-sectional view of one embodiment of a catheter assembly having an EAP shown disposed over balloon waist.
Figure 11B:
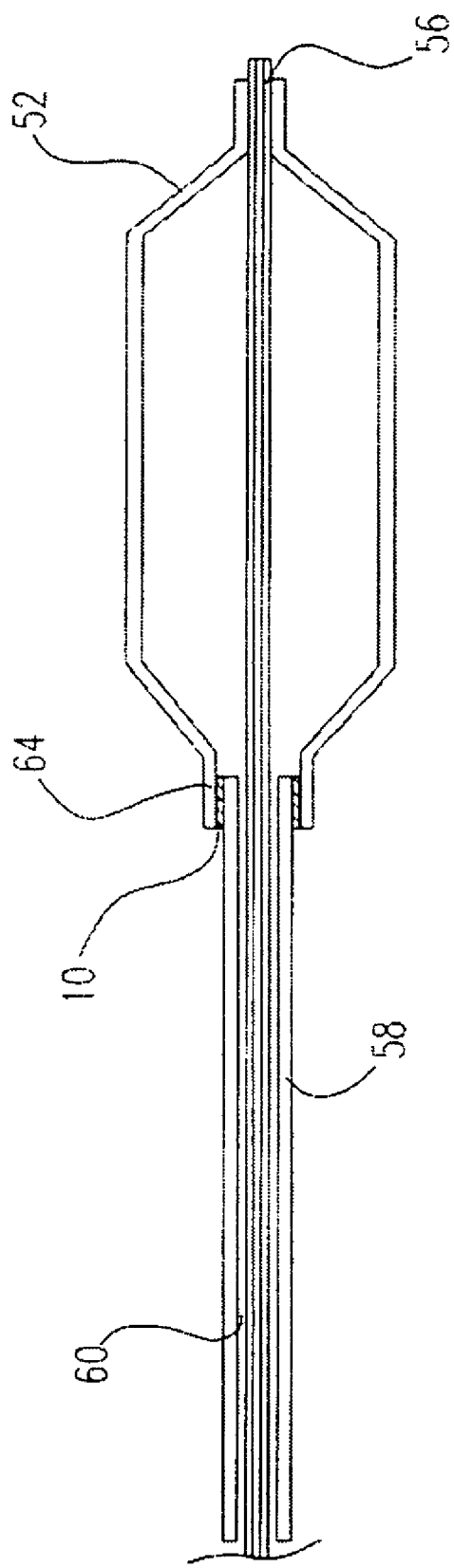
FIG. 11b is a longitudinal cross-sectional view of one embodiment of a catheter assembly with EAP disposed on the outer shaft between outer shaft and balloon waist.
Figure 11C:
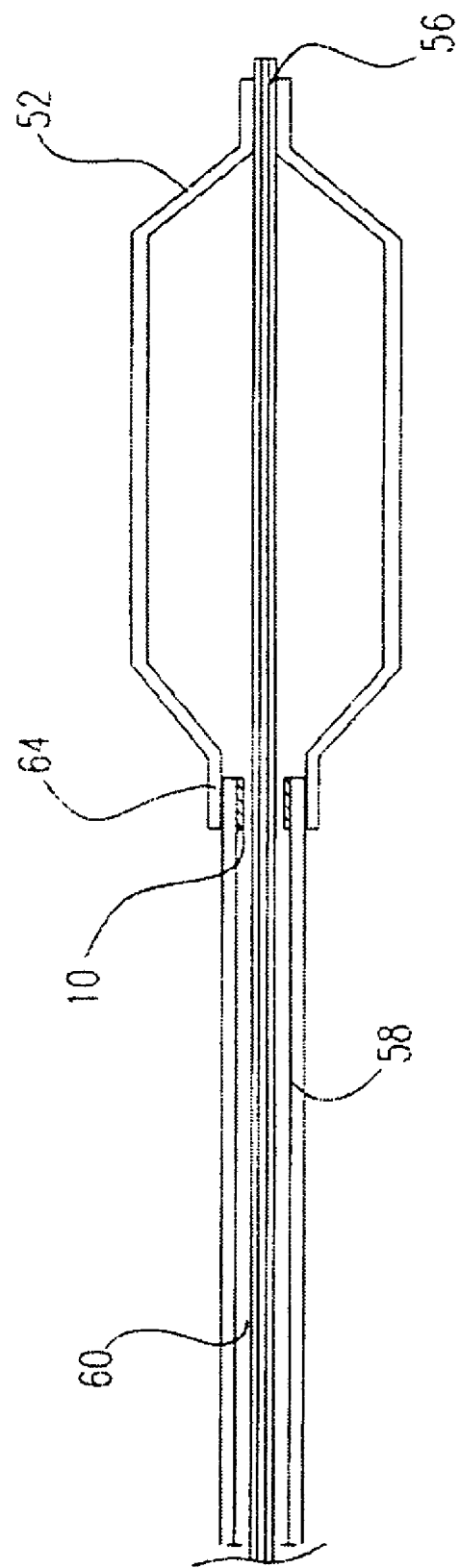
FIG. 11c a longitudinal cross-sectional view of one embodiment of a catheter assembly with EAP disposed on the inner shaft between inner and outer shaft at the distal end of outer shaft.

Balloon member 52 may be secured to outer tube 58 of shaft assembly using any techniques known in the art. One technique involves a laser weld of balloon member 52 at the proximal waist 64 of the balloon member 52 to the distal end of the outer tube 58. In the embodiment shown in FIGS. 11a-11c, EAP active region 10 is shown disposed at the weld region on balloon waist 64 in FIG. 11a, on the distal end of the outer shaft 58 between balloon waist 64 and outer shaft 58 in FIG. 11b, and on the inner shaft 56 between the distal end of outer shaft 58 and inner shaft 56 in FIG. 11c. All views 11a-11c are shown as longitudinal cross-sections of the catheter assembly. In any of these embodiments, the EAP active region 10 can be activated to contract or expand to control inflation/deflation of the balloon by stopping (contraction) or allowing (expansion) expansion fluid to flow through the inflation lumen 60.

Figure 12:
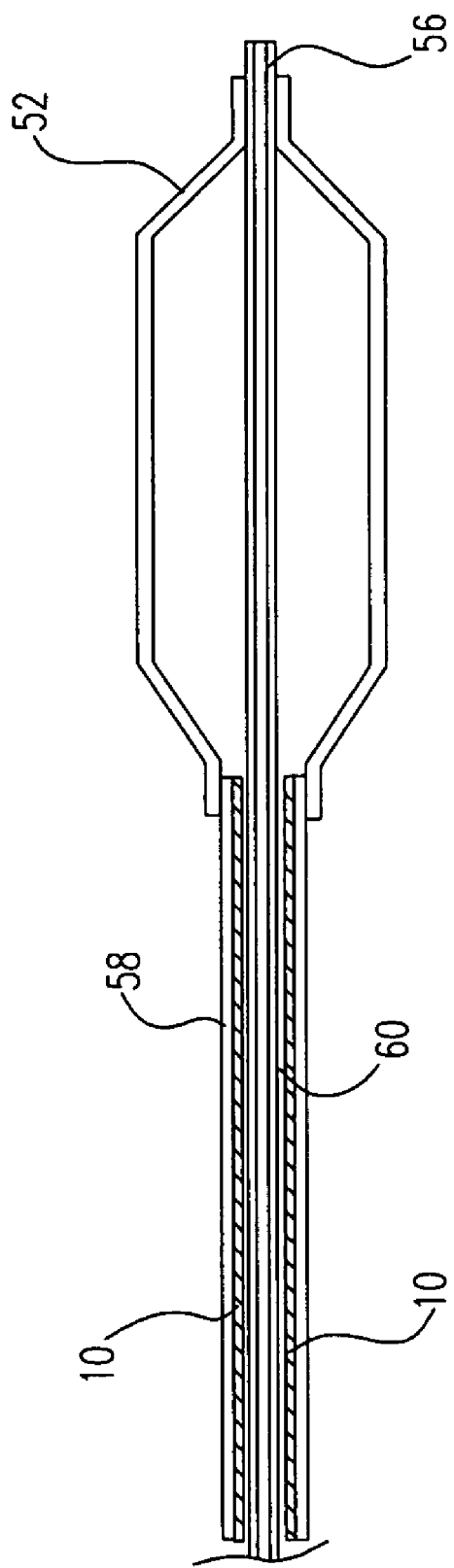
FIG. 12 is a longitudinal cross-sectional view of one embodiment of a catheter assembly having EAP active region disposed on outer shaft.

FIG. 12 is a longitudinal side view of the distal end of the catheter assembly 25 of FIG. 10 showing the expandable balloon member 52 secured to outer catheter shaft 58 at the proximal end of the balloon and secured to the inner catheter shaft 56 at the distal end of the balloon. Additionally, catheter shaft assembly 50 (FIG. 1) is shown having an EAP actuator 10 disposed on the inner surface of the outer catheter shaft 58 for aiding in shaft properties such as shape, bending an stiffness. Control of such properties using an EAP actuator 10 in accordance with the invention can aid in delivery of a catheter assembly through a patient's body lumen.

Figure 13:
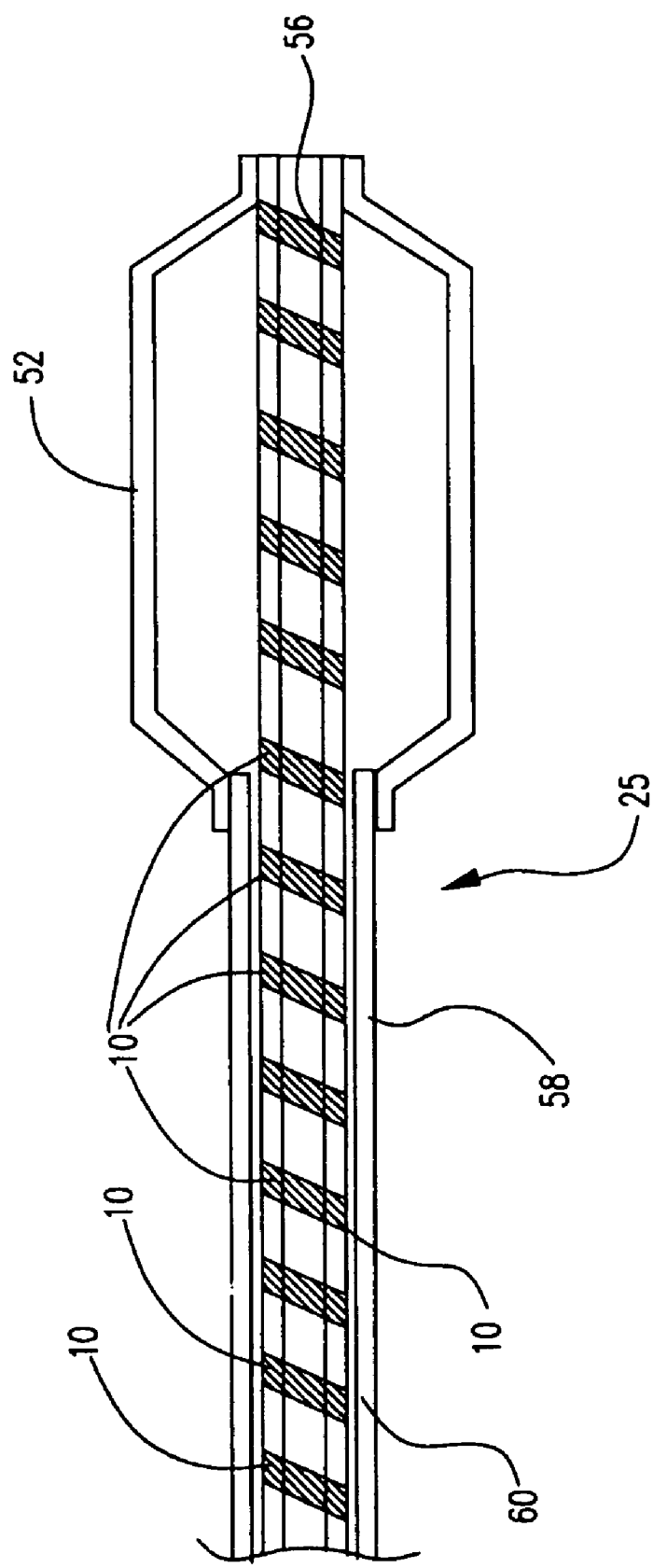
FIG. 13 is a longitudinal cross-sectional view of one embodiment of a catheter assembly having EAP positioned on the inner catheter shaft in a spiral wrap.

FIG. 13 illustrates an embodiment wherein inner tube 56 of catheter assembly has EAP active region 10 disposed in a helical or spiral pattern thereon for providing inner tube 56 with a twist. EAP active region 10 can be selectively activated so as to twist the inner to improve balloon rewrap, to provide rotation during crossing of a lesion, or to align the assembly within a side branch lumen, such as in the case of a bifurcated catheter assembly (not shown). For either POBA (plain old balloon angioplasty) or for stent delivery, the balloon will be inflated during use, either to compress the plaque stenosis to the vessel wall, or for expansion of the stent. A negative pressure is then applied to the balloon for deflation. Alternatively, the spiral configuration may be replaced with rings of EAP active regions uniformly spaced at a predetermined distance along the inner shaft. Providing an inner shaft with a twist for improving balloon rewrap is disclosed in commonly assigned copending U.S. patent application Ser. No. 11/282,252, filed Nov. 18, 2005, the entire content of which is incorporated by reference herein.

While expandable balloons are typically collapsible, they may not always collapse as desired and may flatten into a "pancake" like shape, rather than to a radially compact minimal cross-section, particularly after inflation to a relatively large diameter. This flattening can increase the possibility that the balloon may interfere with the arterial wall during balloon withdrawal or when being placed across a second stenosis. This pancake-like balloon shape can increase the difficulty of withdrawal after inflation.

EAP active region 10 by providing the inner with a twisting motion, can facilitate rewrap of the balloon to a smaller profile about the catheter shaft.

Figure 14:
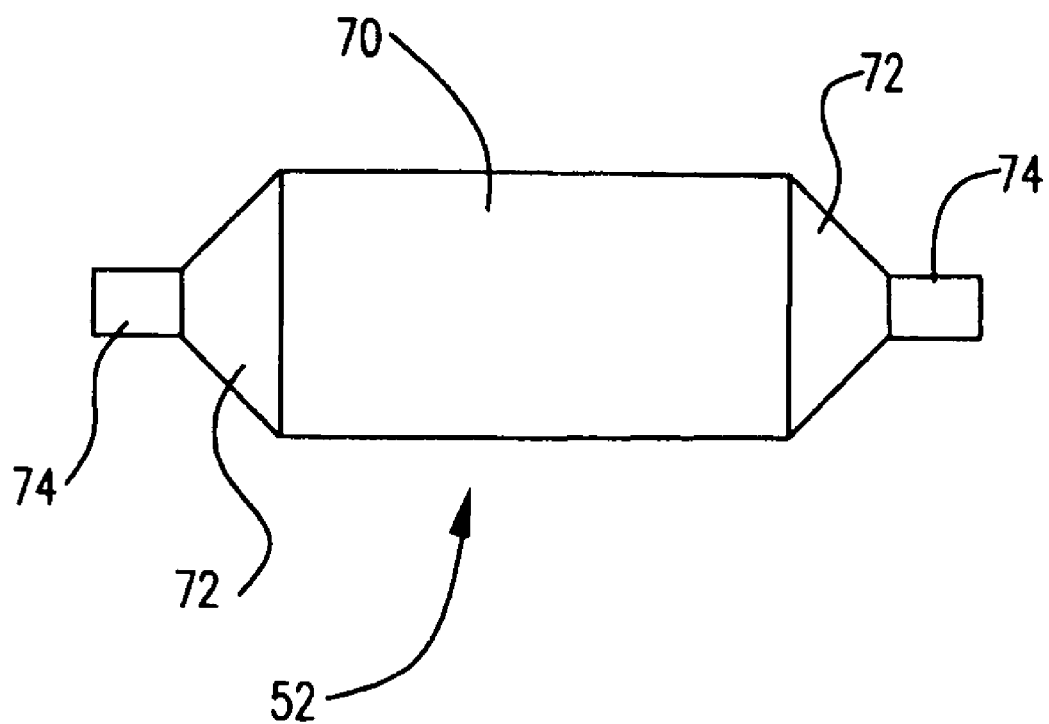
FIG. 14 is a perspective side view of an embodiment of an expandable medical balloon.

The expandable balloon member according to the invention may be formed using a variety of balloon configurations. One typical configuration is a balloon 52 as shown in perspective in FIG. 14 having a body portion 70, cone portions 72 and waist portions 74.

In use, a balloon, disposed about the distal end of a catheter assembly, as shown in FIG. 10, may be delivered to the site of a lesion and expanded to push plaque or other obstruction outward and improve flow through a vessel. An implantable medical device such as a stent may be disposed about the end of the balloon, and the balloon used to deliver the stent to a lesion site. Once there, the balloon is expanded, expanding the stent. The balloon is then deflated and pulled from the expanded stent.

Using EAP active regions strategically positioned on an expandable balloon member according to the invention, a variety of balloon characteristics useful in such applications may be improved.

Furthermore, as illustrated by the following FIGS. 15A-15F and FIGS. 16A-16B, the EAP active regions can be positioned selectively on an expandable medical balloon to benefit both POBA (plain old balloon angioplasty) applications and in applications where the expandable medical balloons are used for delivery of medical devices such as for stent delivery systems (SDS).

Figure 15A:
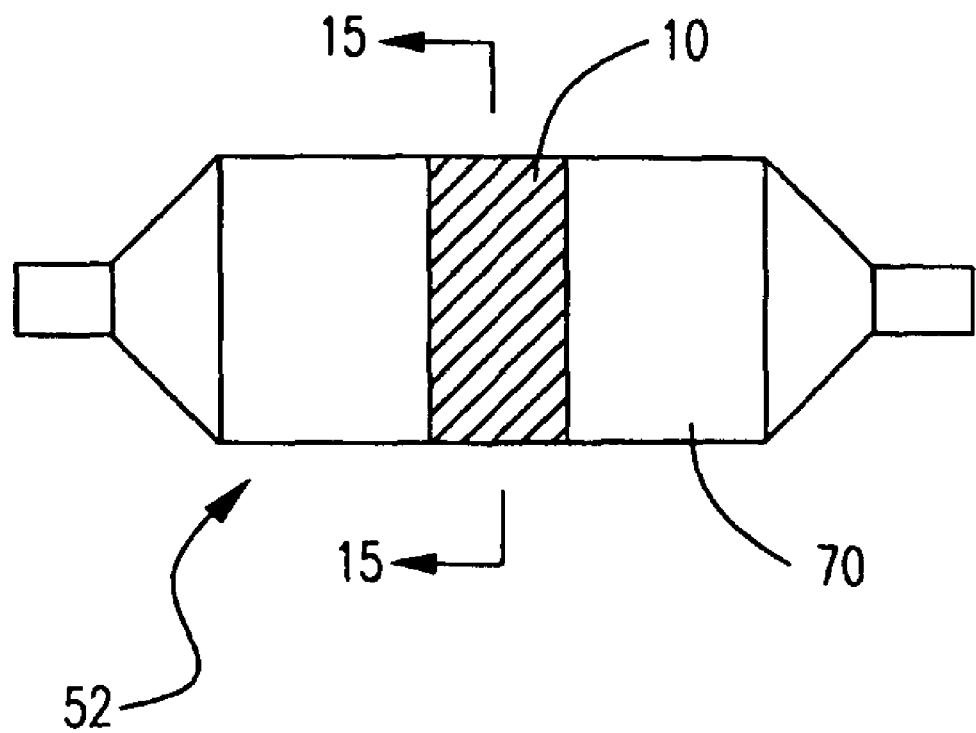
FIG. 15A is a side view of an embodiment of an expandable medical balloon having an EAP active region on the balloon body.
Figure 15B:
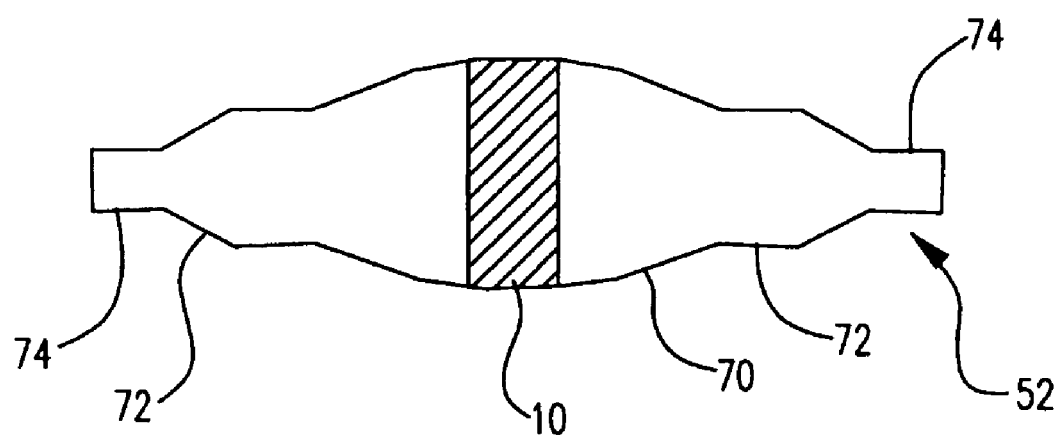
FIG. 15B is a side view of an embodiment of an expandable medical balloon similar to that shown in FIG. 15A with a center-up deployment.
Figure 15C:
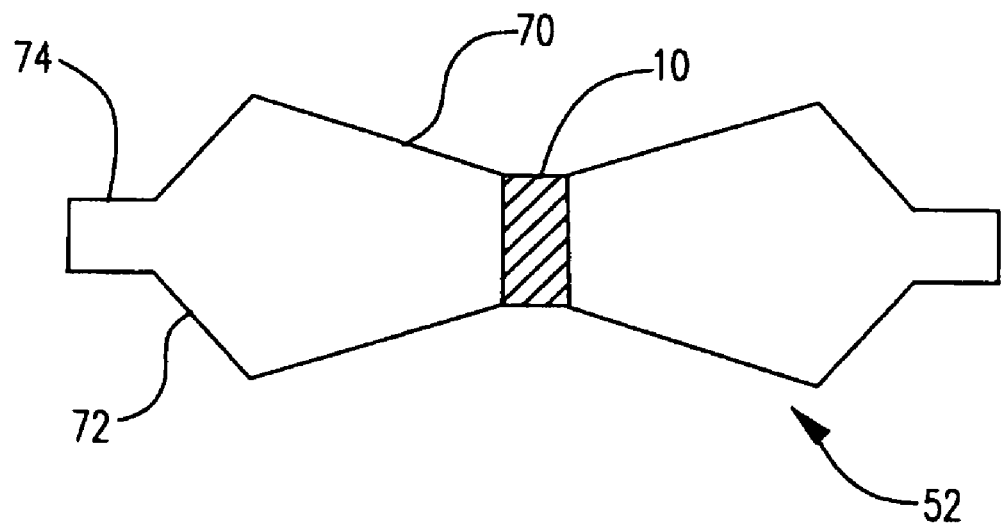
FIG. 15C is a side view of an embodiment of an expandable medical balloon similar to that shown in FIG. 15A in a partially deflated state.

FIG. 15A is a side view illustrating the strategic positioning of an EAP active region 10 on the central portion of balloon body 70. This allows for precisely controlling center-up balloon deployment as illustrated in FIG. 15B. Furthermore, during deflation, the EAP region 10 may be activated to contract wherein the center portion of the balloon will deflate first as shown in FIG. 15C. This can be beneficial when expandable balloon 52 is employed for delivery of implantable medical devices such as stents.

Figure 15D:
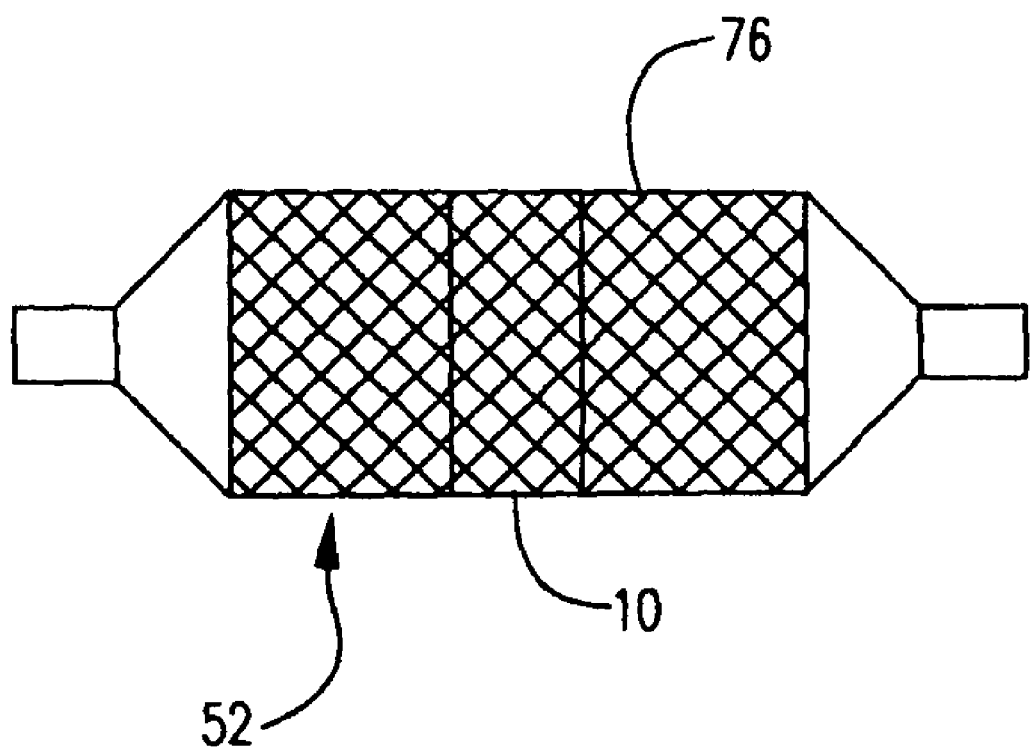
FIG. 15D is a side view of an embodiment of an expandable medical balloon similar to that in FIG. 15 having a stent mounted thereon.

The balloon shown in FIG. 15A can be advantageously employed for delivery of implantable medical devices, e.g. stent delivery, as well. FIG. 15D is a side view of a balloon similar to that shown in FIG. 15A having a stent mounted thereon.

Figure 15E:
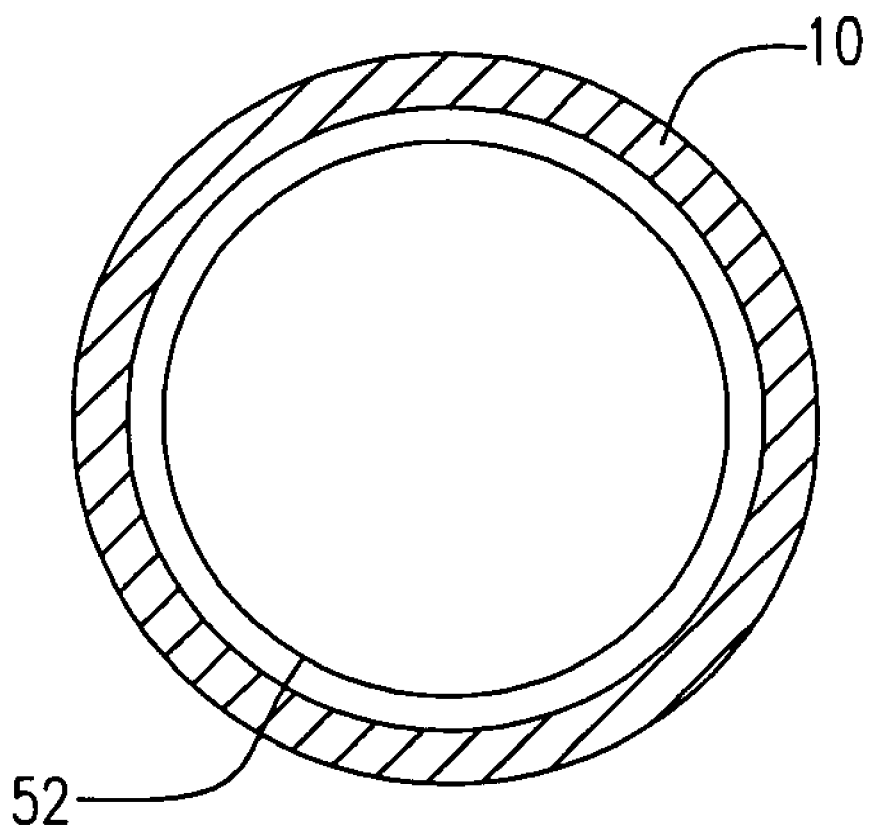
FIG. 15E is a radial cross-section taken at section 15-15 in FIG. 15A
Figure 15F:
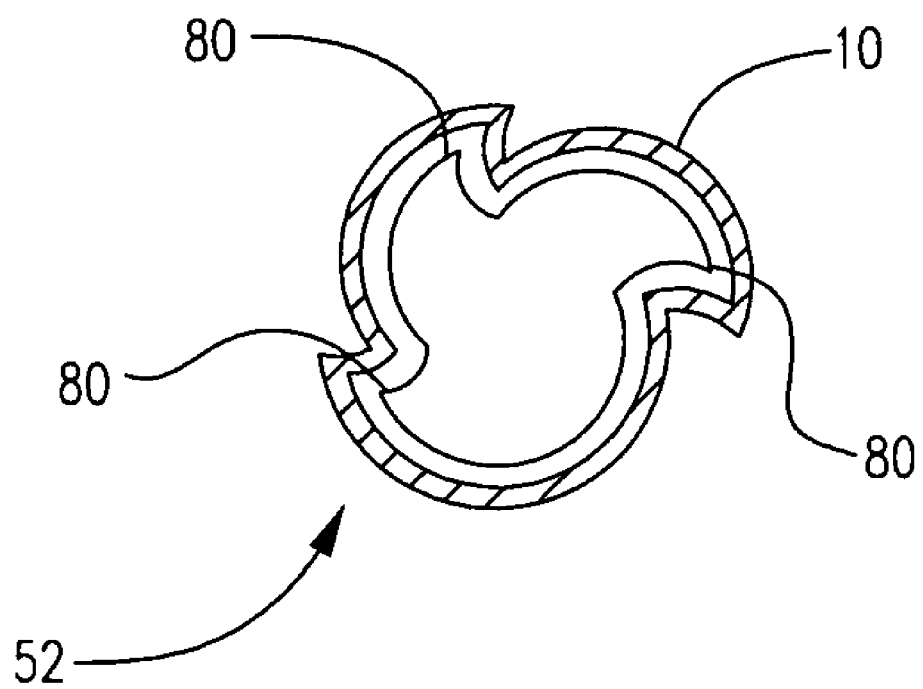
FIG. 15F is a radial cross-section of a balloon similar to that shown in FIG. 15E in a folded configuration wherein the balloon has a three-wing configuration.
Figure 18A:
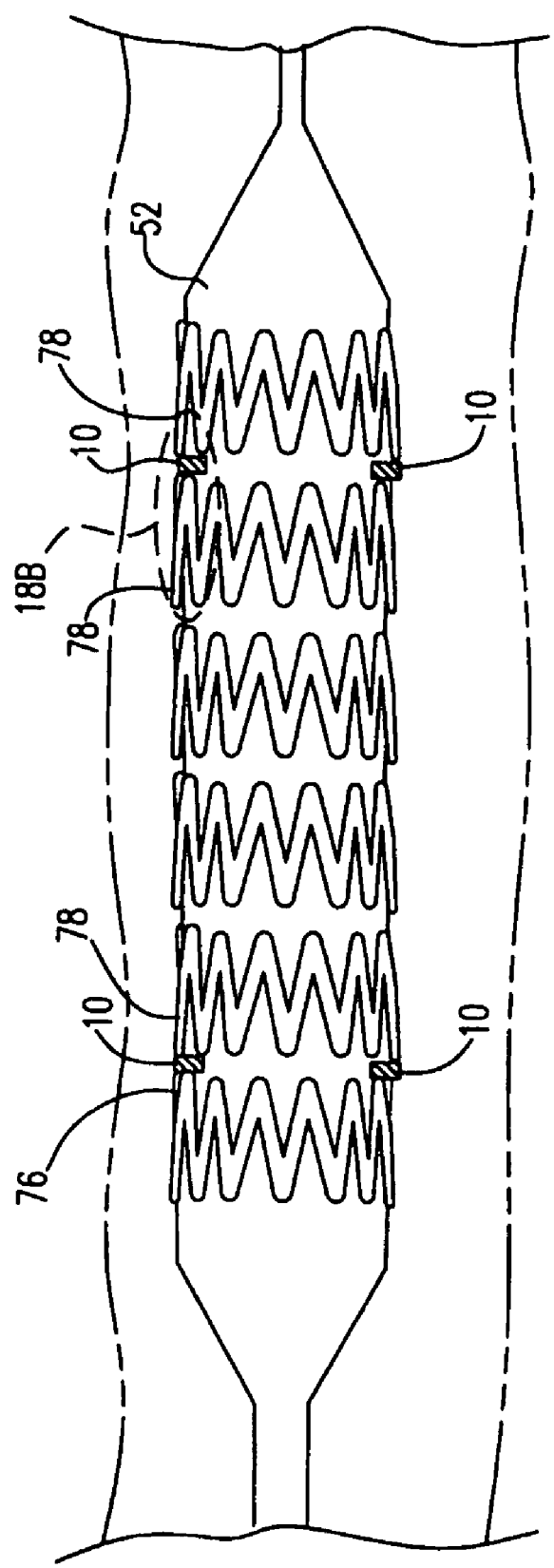
FIG. 18A is a side perspective view of a balloon having a stent mounted thereon with EAP active regions employed for stent securement.

FIG. 15E is a radial cross-section, taken at section 15-15 in FIG. 15A. FIG. 15F is a radial cross-section of the balloon as shown in FIG. 15 taken at section 15-15 in FIG. 15, but is shown in a folded state, the balloon having three wings 80. The particular embodiment shown in FIG. 18 shows a balloon having three wings and is for purposes of illustration only. Balloons may be formed having two, four, five, six, etc. wings as well. Strategic positioning of the EAP active regions on the balloon body can also facilitate deflation, and improve folding or rewrapping characteristics which is discussed more below.

In another alternative embodiment, the EAP active regions 10 are positioned on the balloon so as to allow for controlled end-up deployment. The EAP active regions can be positioned at one end or the other, or both ends as desired for controlling deployment.

Figure 16A:
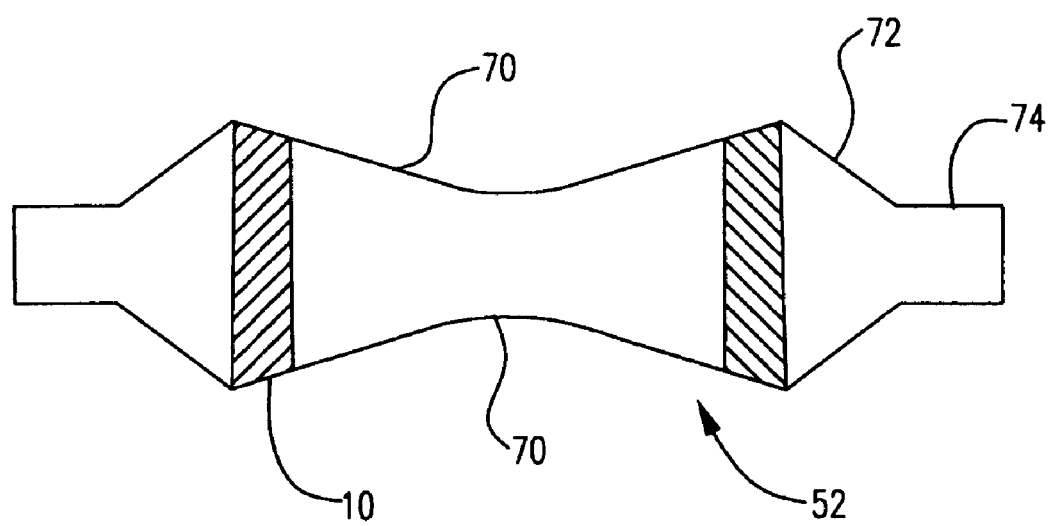
FIG. 16A is a side view of an alternative embodiment of an expandable medical balloon with EAP active regions positioned for end-up balloon deployment.

FIG. 16A is a side view of a balloon having EAP active regions 10 positioned on the end portions of the body region 70 of balloon 52. Expansion of the EAP active regions 10 can result in an end-up deployment.

Figure 16B:
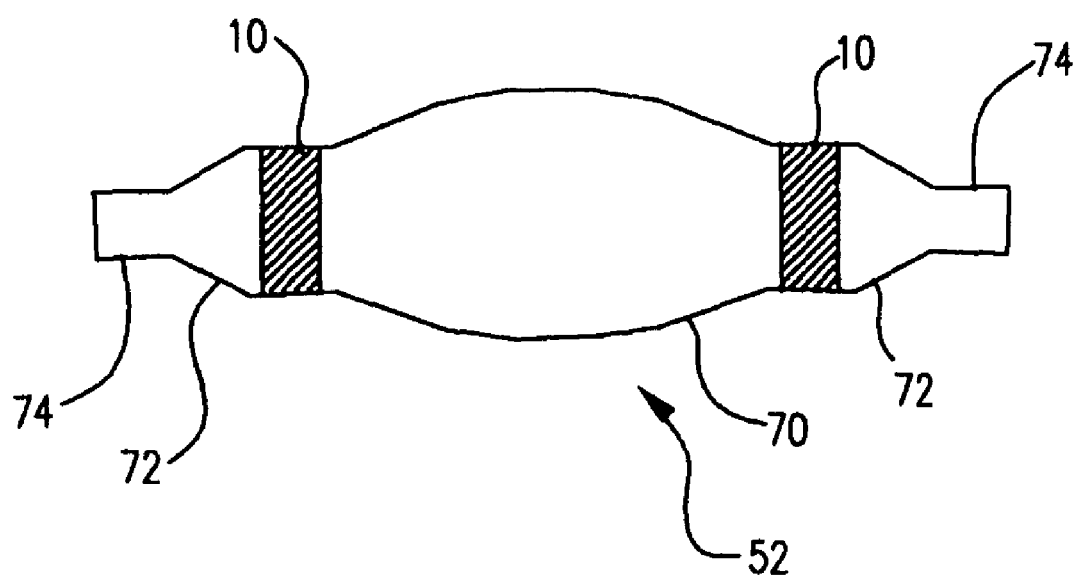
FIG. 16B is a side view of a balloon similar to that in FIG. 16A illustrating center-up deployment with contraction of EAP active regions.

Alternatively, contracting the EAP active regions 10 during balloon expansion, can allow for a center-up balloon deployment as is shown in FIG. 16B.

Figure 16C:
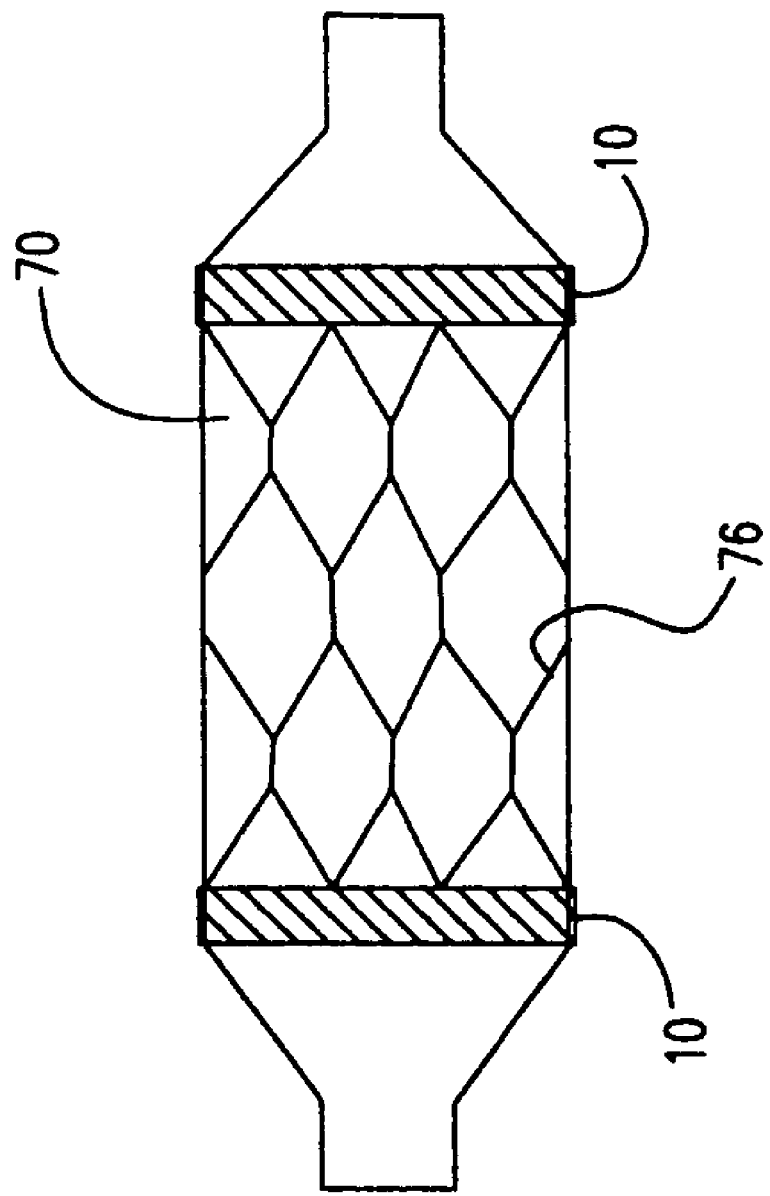
FIG. 16C is a side view of a balloon similar to that shown in FIG. 16A an 16B further in combination with a stent.

Positioning of EAP active regions 10 on the end portions of the balloon body 70, can be advantageously employed for stent delivery. FIG. 16C is a side view of a balloon 52 having EAP active regions 10 located on the end portions of the balloon body 70 shown with a stent 76 positioned there between. When activated, EAP active regions 10, are expanded, resulting in a raised region to keep the stent positioned more securely on the balloon. The EAP active regions can be deactivated, contracted, for stent deployment which can also facilitate balloon deflation. The EAP active regions 10 are shown in an activated, expanded state in FIG. 16C.

Figure 16D:
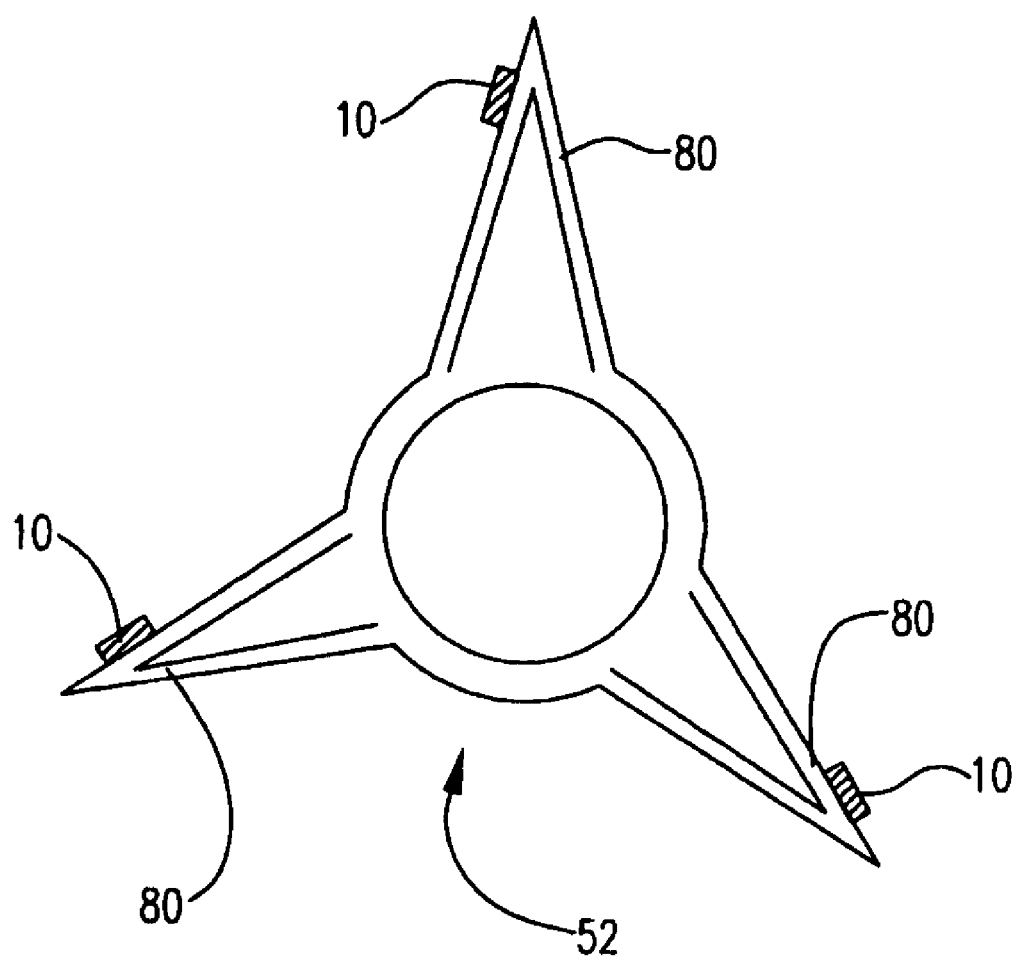
FIG. 16D is a radial cross-section of a balloon having three-wing configuration, with small regions of EAP disposed on each wing.
Figure 16E:
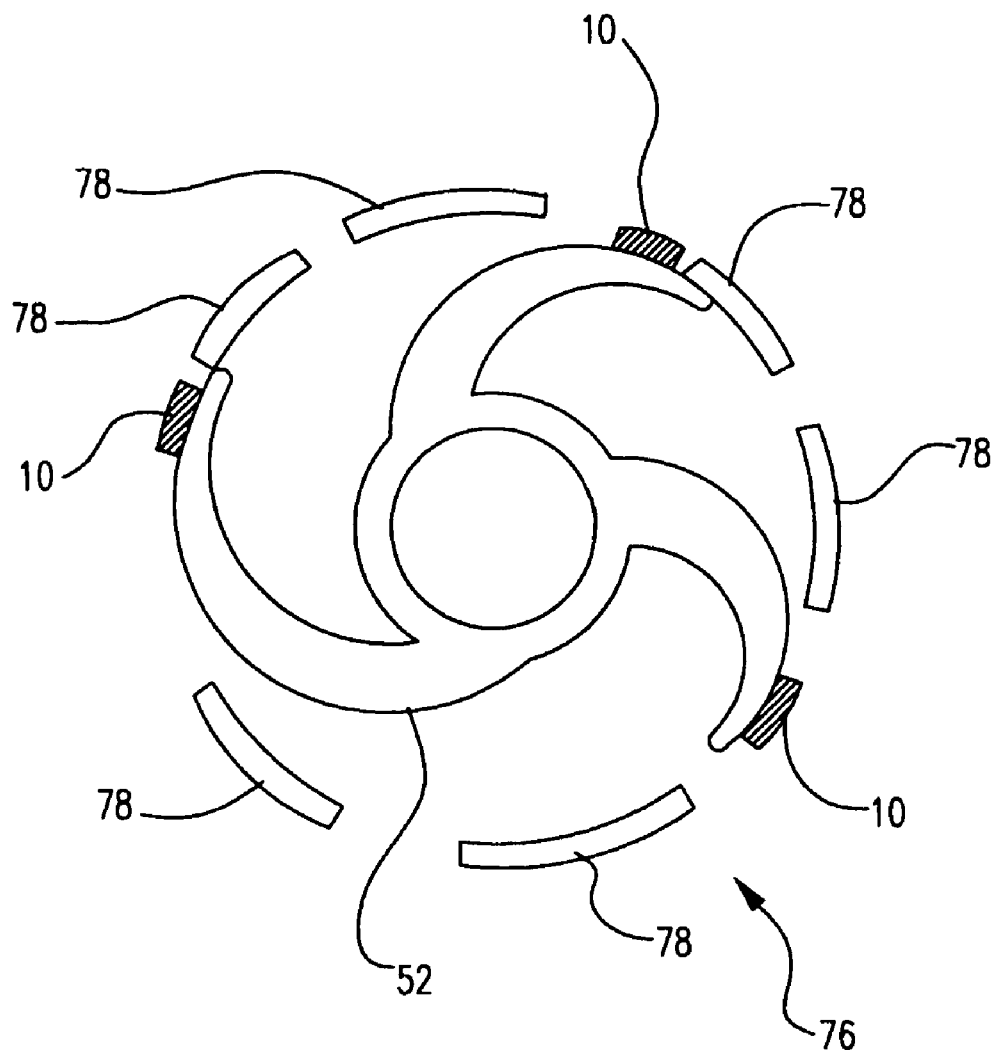
FIG. 16E is a radial cross-section of a balloon similar to that shown in FIG. 16D with the wings wrapped about the longitudinal axis and a stent disposed thereon.

Typically, the stent is crimped onto the balloon when the balloon is in a folded configuration. The balloon will typically first be formed into a two-wing, three-wing, four-wing, five-wing, six-wing, etc. configuration. A radial cross-section of a balloon having three-wing configuration, with small regions of EAP 10 disposed on each wing is shown in FIG. 16D. Actuation of each EAP region 10 can aid in balloon folding/rewrapping. The balloon 52 is further shown with the wings wrapped about the longitudinal axis of the balloon 52 as shown in FIG. 16E and having a stent disposed thereon. EAP active regions 10 are shown positioned between stent struts 78.

Figure 17:
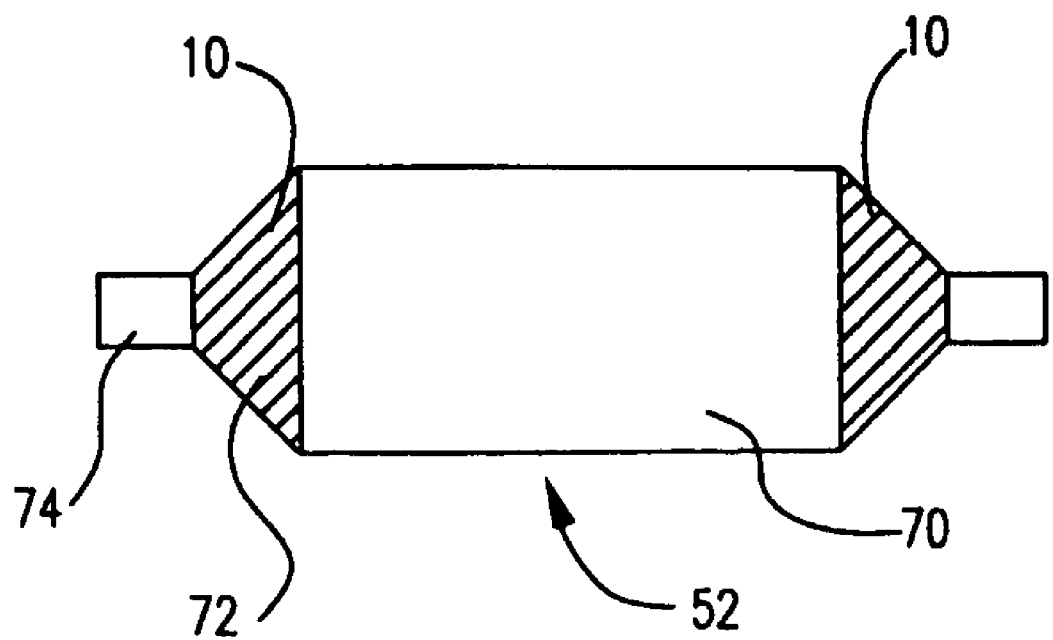
FIG. 17 is a side view of a balloon having EAP active regions positioned on the cone portions of the balloon.

While FIG. 16B illustrates an embodiment wherein the EAP active region is positioned on the end portions of the body region 70 of balloon 52, EAP active regions 10 may also be positioned on the cone portion 72 only as shown in FIG. 17. Contraction of the EAP active regions 10 during balloon inflation can also result in a center-up balloon deployment. The strategic positioning of the EAP active regions on the cones 72 can also be beneficial for stent delivery. A stent is typically not crimped over the cone portions 72 of the balloon, but only over the body portion 70 (see FIG. 14). During balloon formation, such as during radial expansion into the balloon mold, the cone portions of a balloon may tend to have a thicker wall than the body portion. The wall thickness of the cones, in combination with the fact that the stent is crimped over only the body portion, can lead to the cones of the balloon expanding before the stent. Thus, adding EAP active regions to the cone portion, can result in better control over the balloon expansion, by contracting the cone regions using EAP, leading in a center up deployment of the balloon and therefore, the cones will not expand prior to the stent. Strategic positioning of the EAP active regions on the end portions of the balloon body or on the cones, can be beneficial for crossing/recrossing of lesions.

Figure 18B:
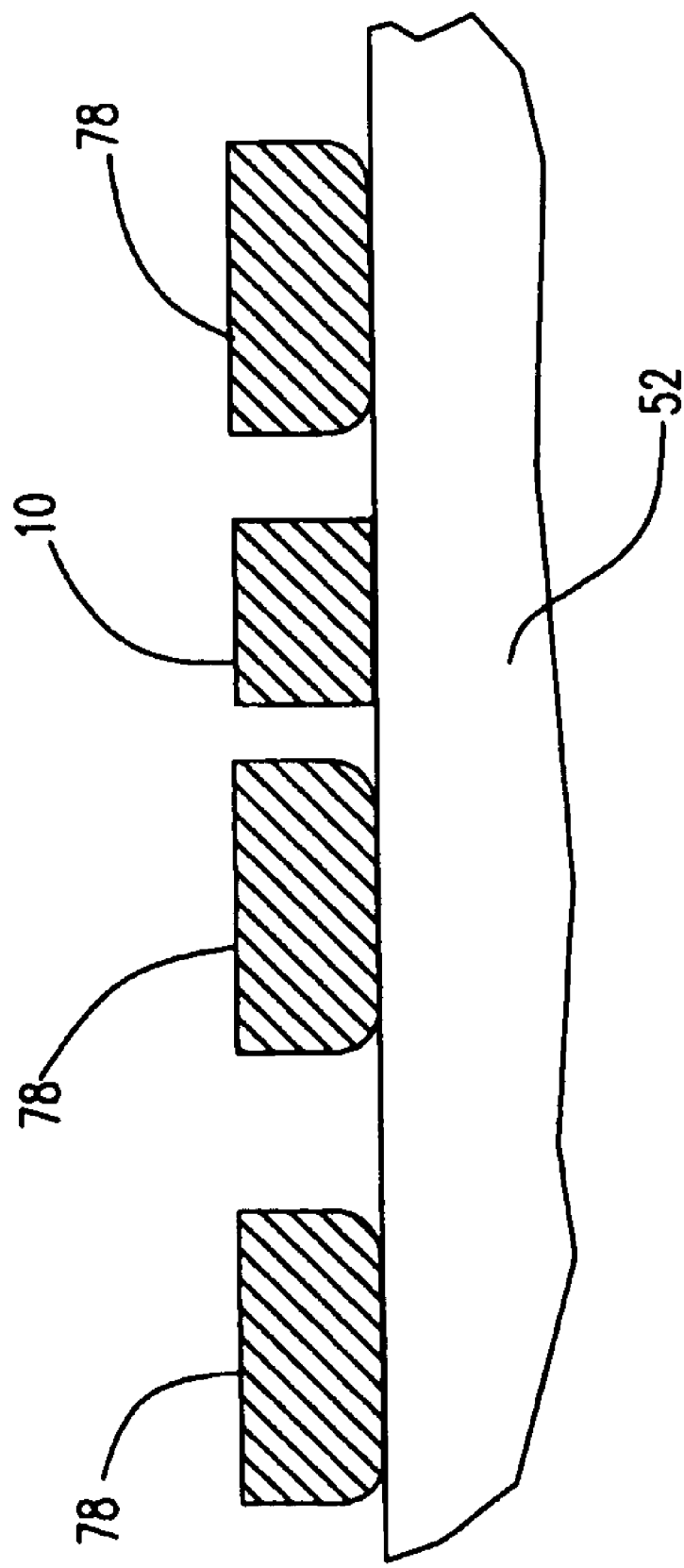
FIG. 18B is an expanded view taken at section 18B in FIG. 18A to more clearly show EAP active regions.

In another embodiment, small EAP active regions 10 are strategically positioned on a balloon 52 so that when a stent 76 is disposed thereon, the EAP active regions 10 are positioned between stent struts 78 as shown in FIG. 18B. The EAP active regions 10 can be activated (expanded) so that they can secure the stent 76 in position until delivery and deployment of the stent. FIG. 18B is an enlarged view taken at 18B in FIG. 18A.

Figure 19:
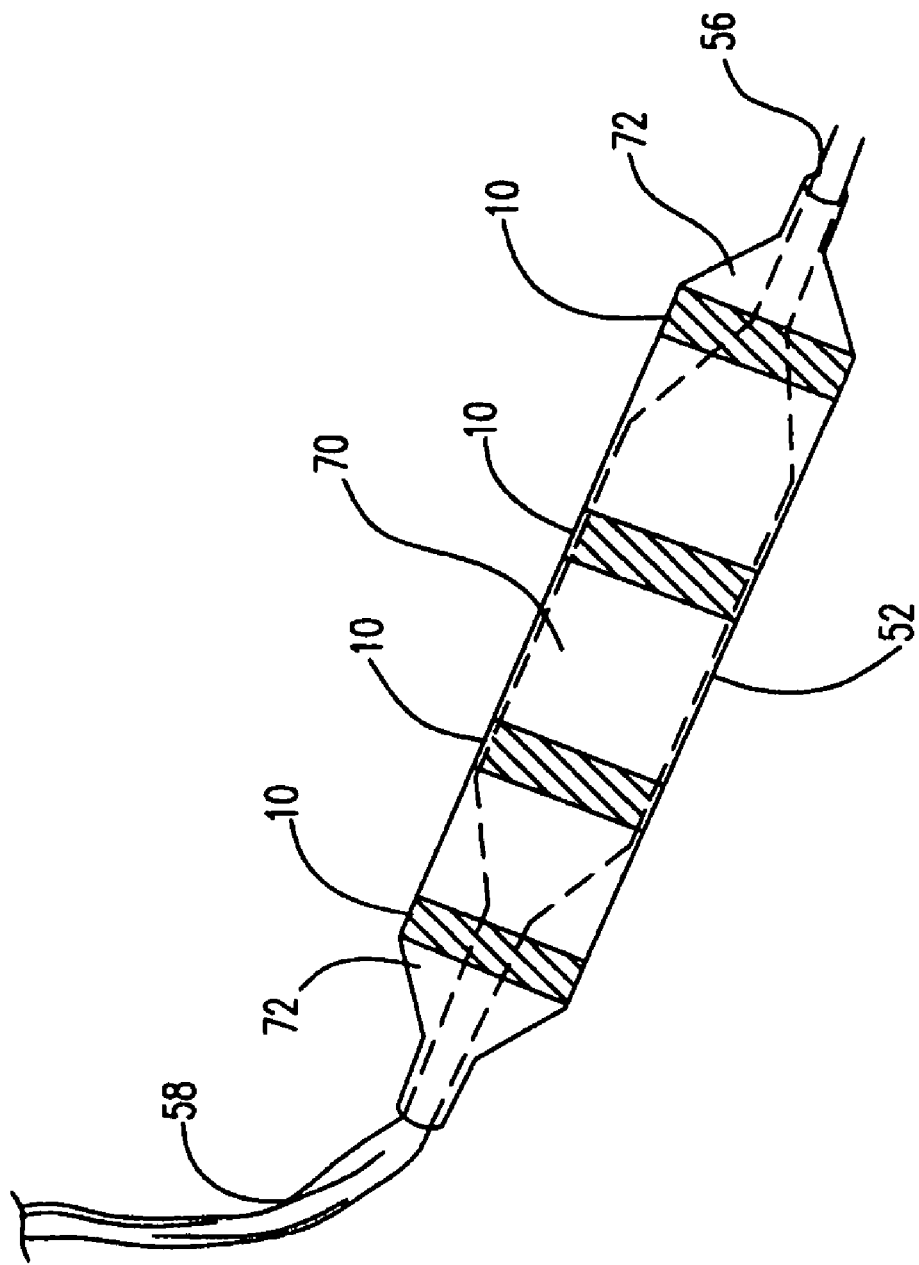
FIG. 19 is a perspective view of an expanded balloon having EAP active regions radially disposed thereon and the deflated balloon shown with ghosting.

In another embodiment, incremental expansion and/or contraction of the balloon member can be achieved by strategically positioning EAP active regions 10 on the cones 72 and/or on the body portion 70 in uniformly spaced distances as shown in perspective in FIG. 19. The EAP active regions 10 may be incrementally expanded and/or contracted via independent control of each active region 10. This may allow the balloon to "crawl" out of a stent (not shown) which has been expanded in a body lumen at a lesion site, for example. The balloon is shown with ghosting in a deflated configuration. In this manner, step-wise activation of the EAP regions can allow for incremental expansion states. Further, step-wise activation of the EAP regions can allow for incremental expansion and/or contraction as well.

Of course, such strategic positioning of the EAP active regions on the outer surface of the balloon body as discussed in any of the embodiments above, can also aid in stent securement by providing a surface which in greater contact with the stent upon activation of the EAP regions to induce expansion.

Figure 20:
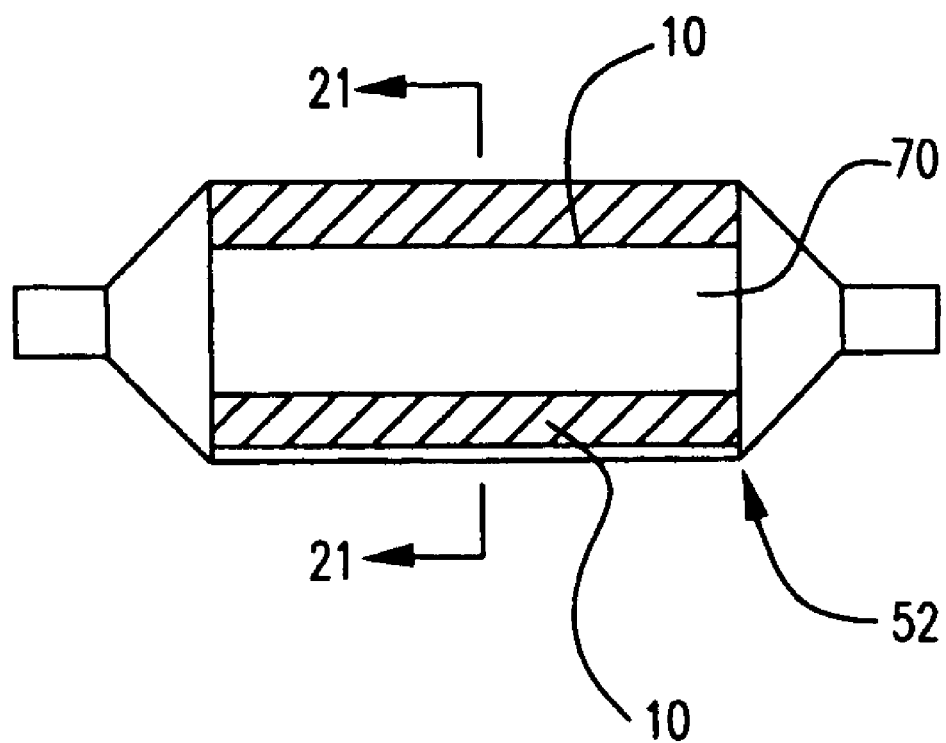
FIG. 20 is a side view of an expandable medical balloon having EAP active regions longitudinally disposed thereon.
Figure 21:
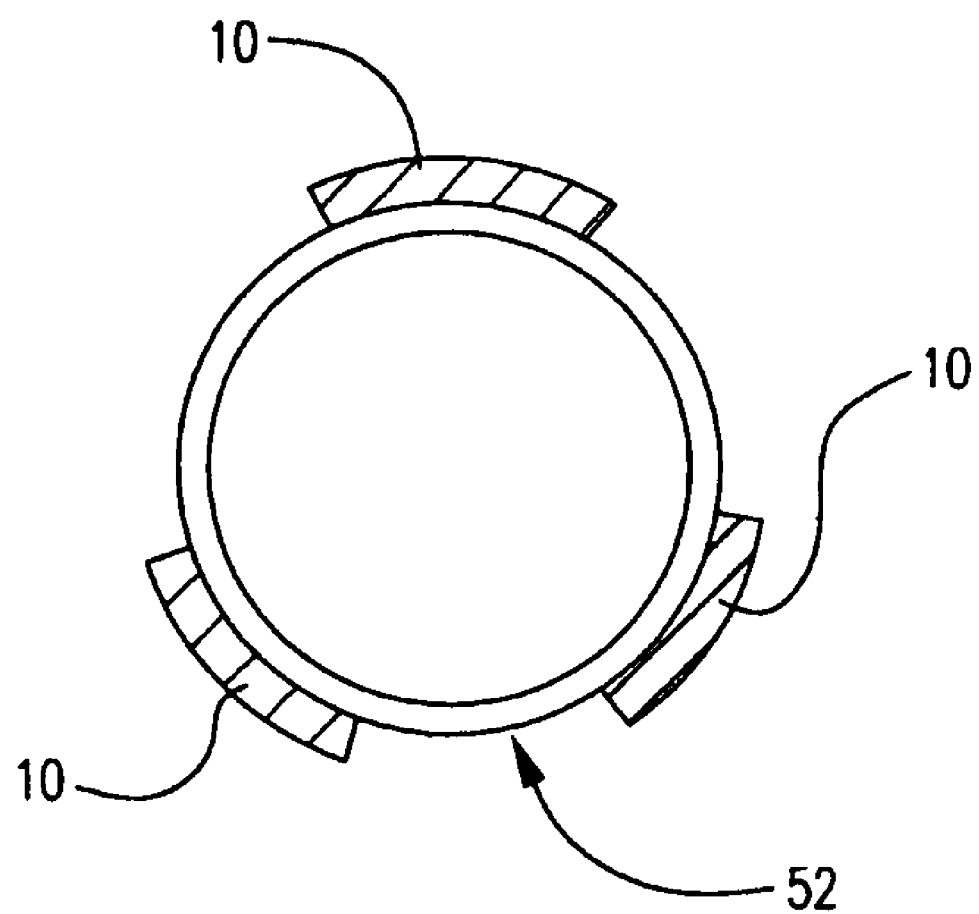
FIG. 21 is a radial cross-section taken at section 21-21 in FIG. 19.

FIG. 20 is a perspective side view of a balloon 52 having longitudinal EAP active regions 10 on balloon body 70. FIG. 21 is a radial cross-section taken at section 21-21 in FIG. 19. These EAP active regions, when actuated, may aid in balloon folding.

Figure 22:
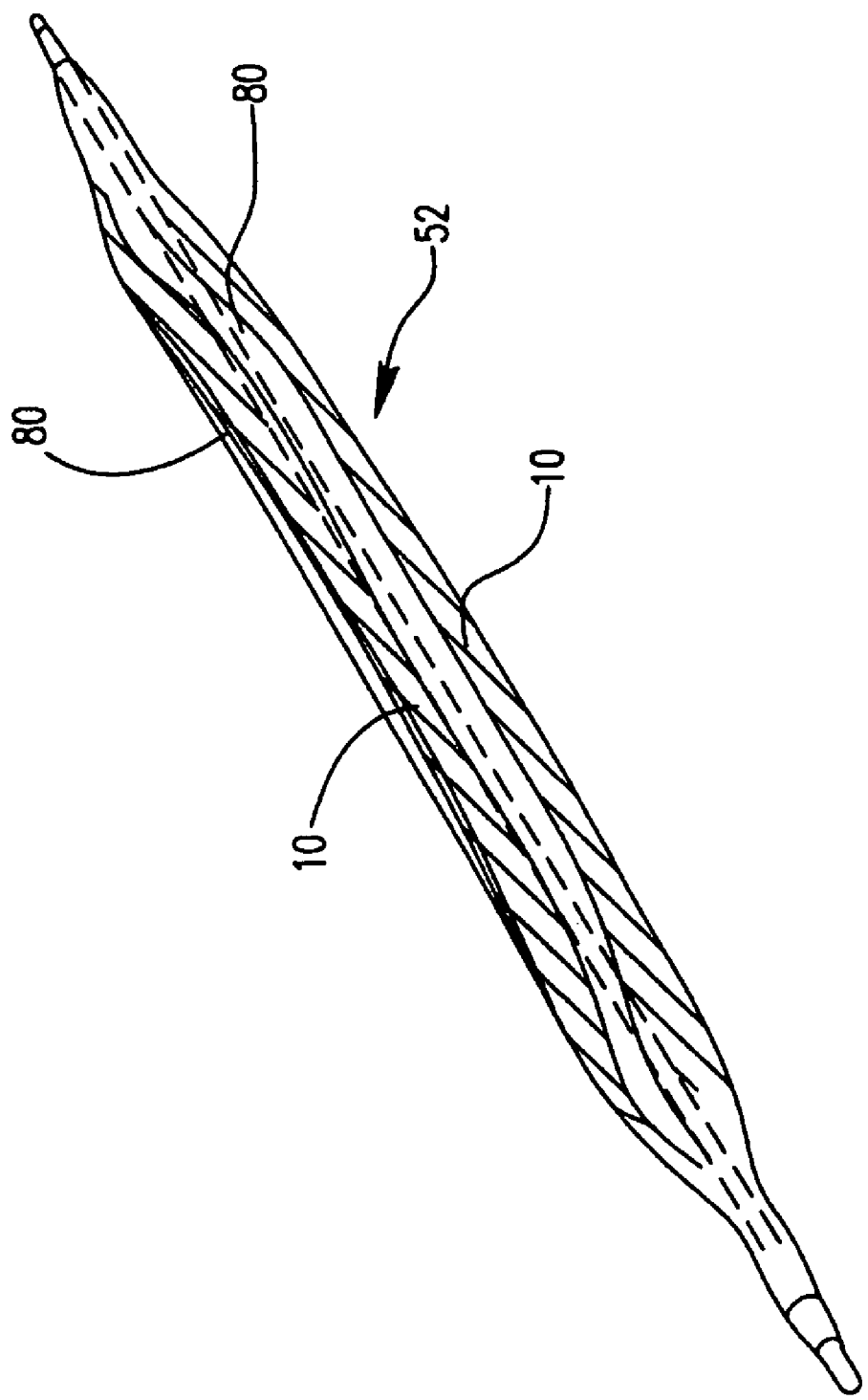
FIG. 22 is a perspective view of a balloon similar to that shown in FIGS. 20-21 in a deflated and folded state.
Figure 23:
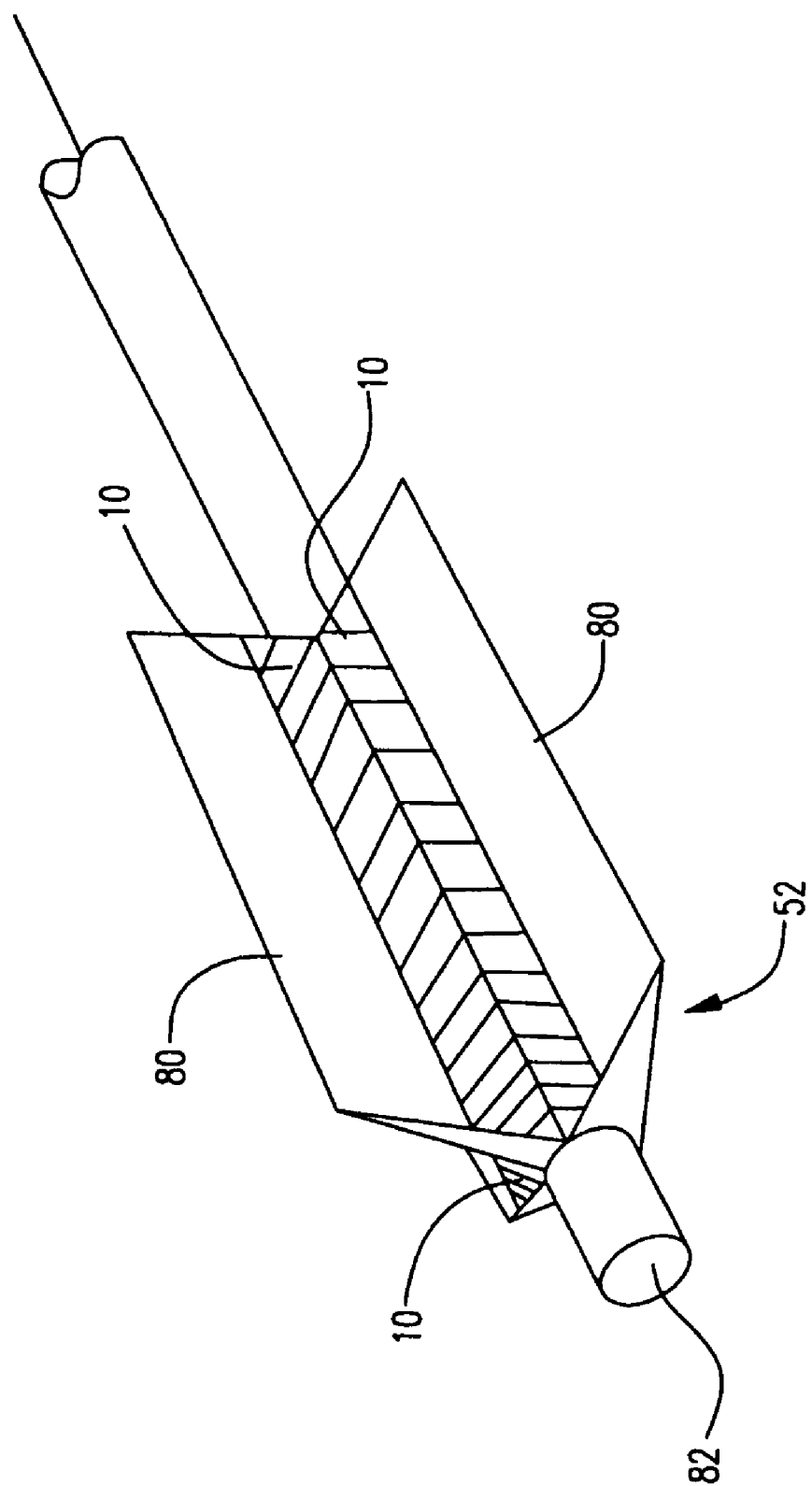
FIG. 23 is a schematic perspective view of a balloon similar to that shown in FIG. 22 prior to wrapping the wings about the longitudinal axis of the catheter assembly.

FIG. 22 is a perspective view of a tri-fold balloon 52 similar to that shown in FIGS. 20-21 in a folded configuration. In this embodiment, the EAP active regions 10 are shown disposed between the balloon folds 80. The placement of the EAP active regions 10 described in this embodiment can be more clearly seen from schematic perspective view of a tri-fold balloon shown in FIG. 23.

Figure 24:
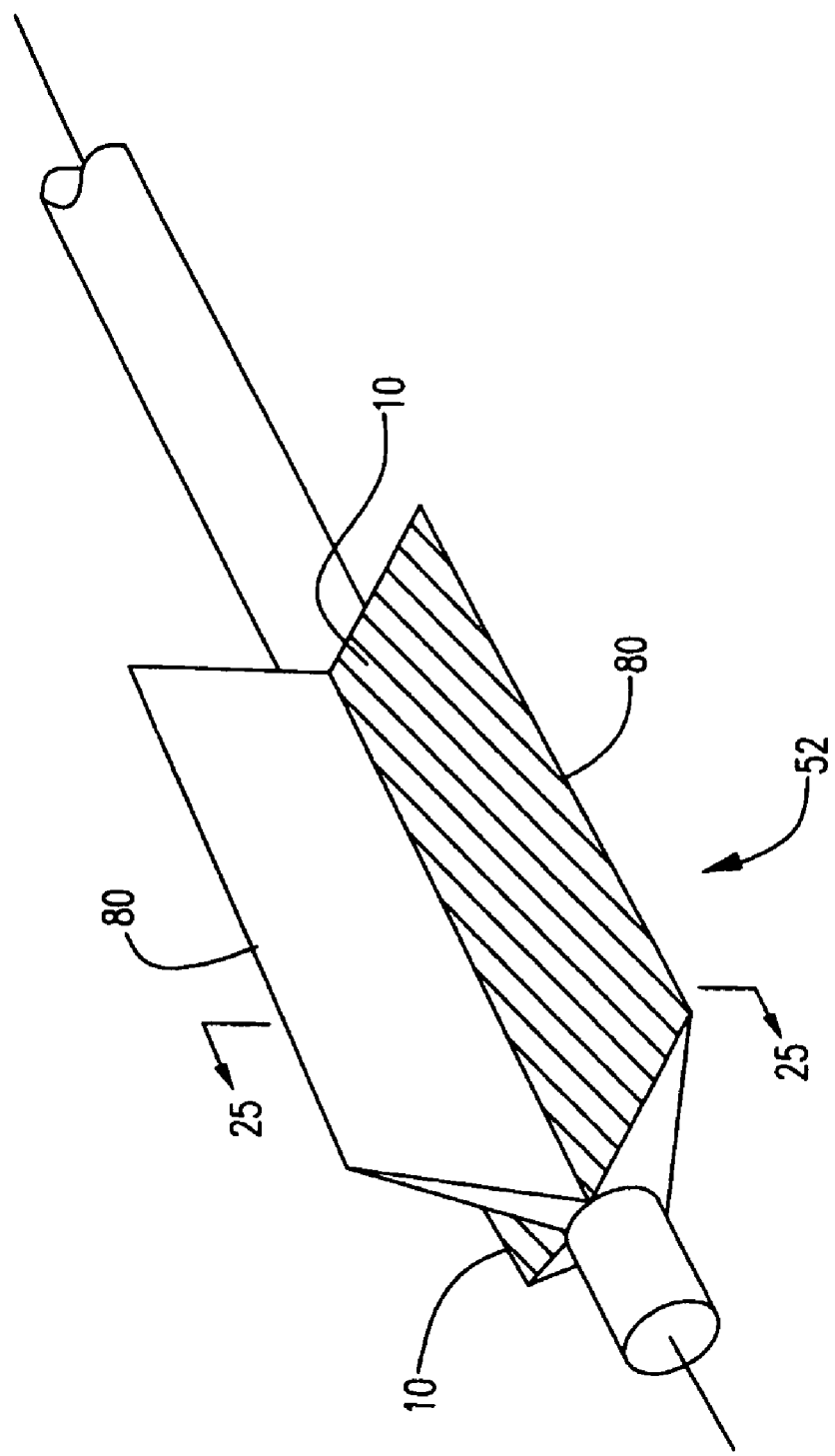
FIG. 24 is a schematic perspective view of a balloon similar to that shown in FIG. 23 having an alternative placement of EAP active regions.
Figure 25:
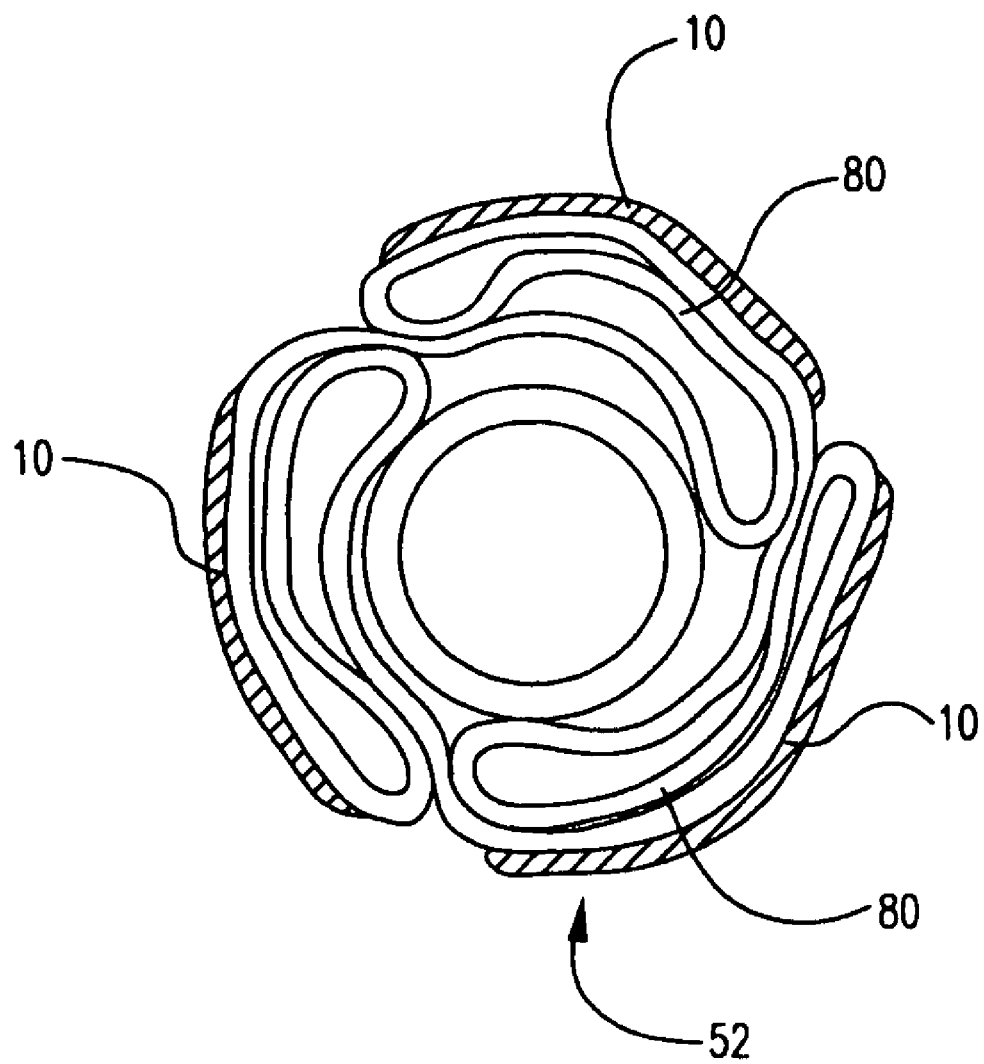
FIG. 25 is a radial cross-section of a balloon similar to that in FIG. 24.

FIG. 24 is a schematic perspective view of a tri-fold balloon 52 illustrating alternative placement of EAP active regions 10 on the balloon wings 80. This strategic placement of the EAP active regions 10 can also aid in folding and rewrap. FIG. 25 is a radial cross-section of a tri-fold balloon similar to that in FIG. 24 taken at section 25-25 in FIG. 24 in a deflated, folded and wrapped configuration.

Figure 26:
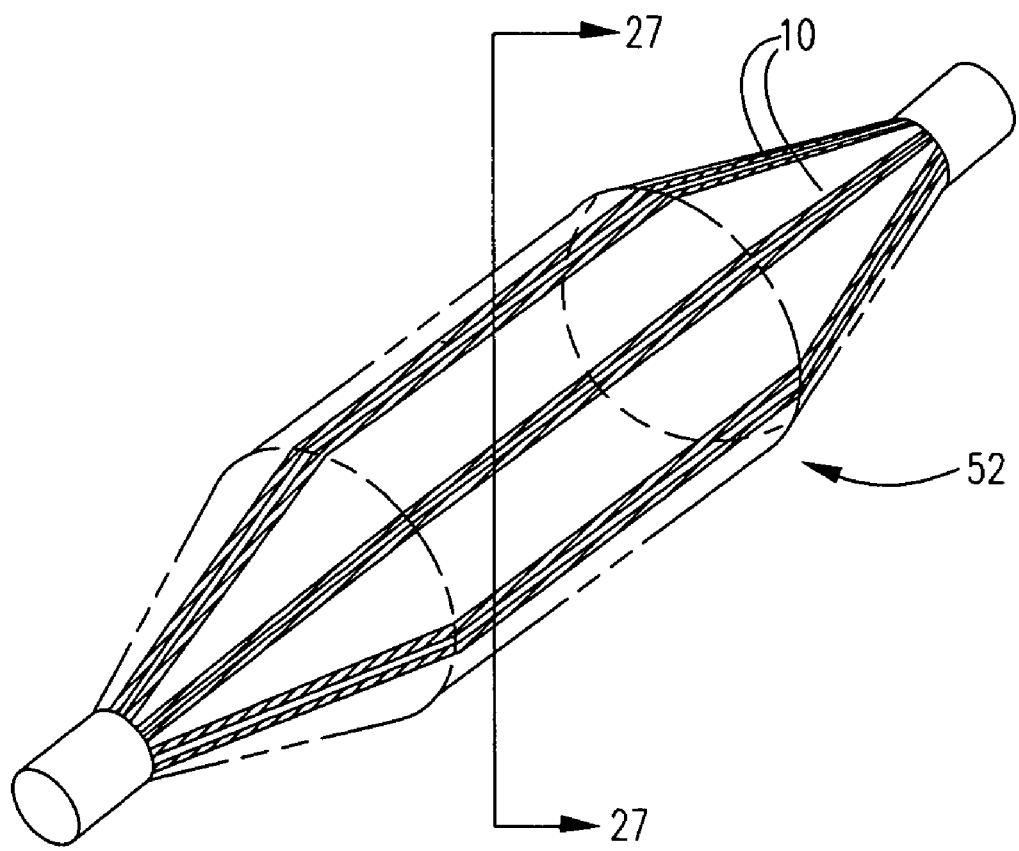
FIG. 26 is a perspective view of a balloon having EAP active regions in phantom, disposed on the inner surface of the balloon.
Figure 27:
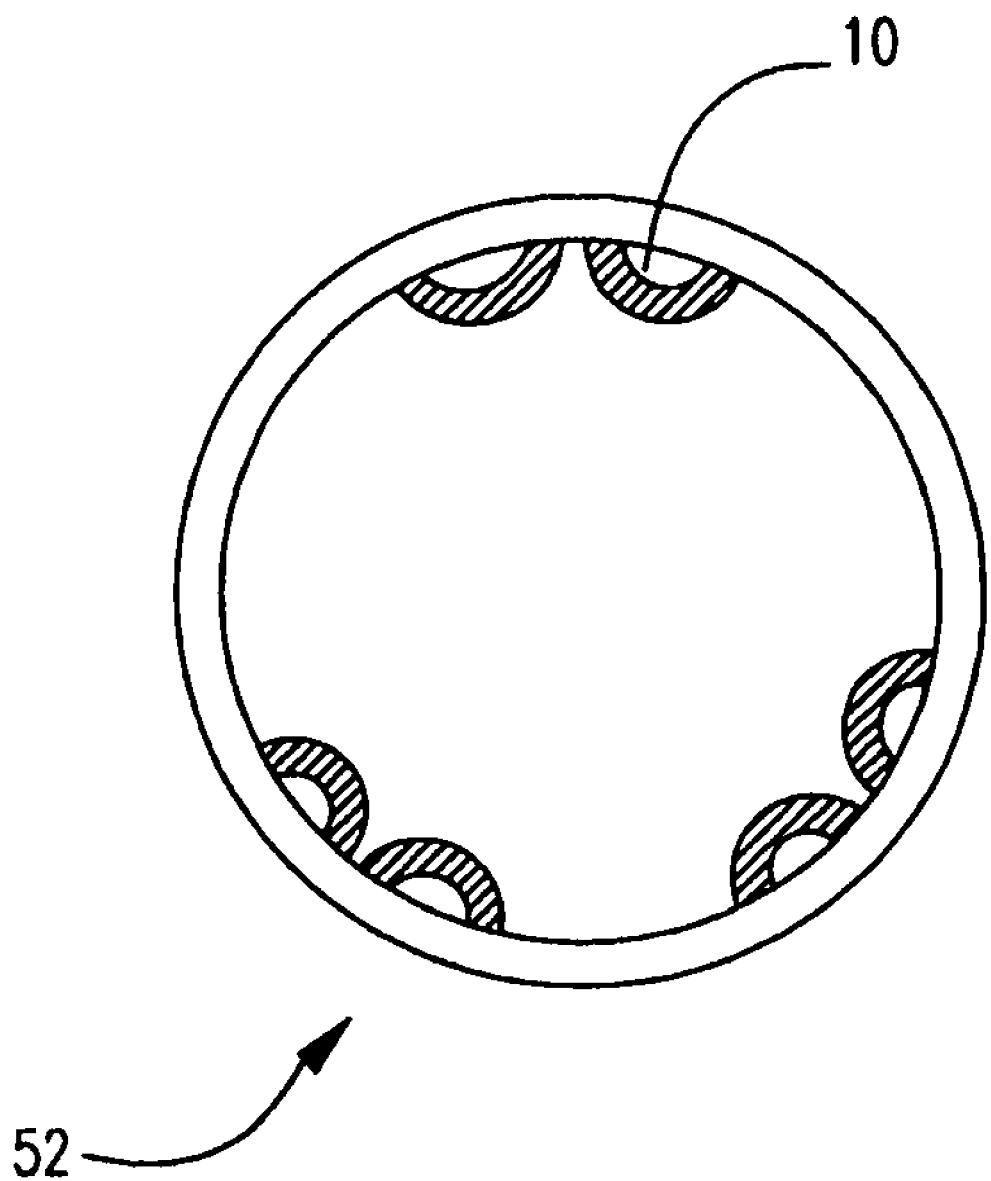
FIG. 27 is a radial cross-section taken at 27-27 in FIG. 26.

Alternatively, the EAP active regions 10 may be disposed on the inner surface of a balloon structure. FIG. 26 is a perspective view of a balloon 52 having strips of EAP active region 10 shown in phantom. FIG. 27 is a radial cross-section taken at 27-27 in FIG. 26.

Figure 28:
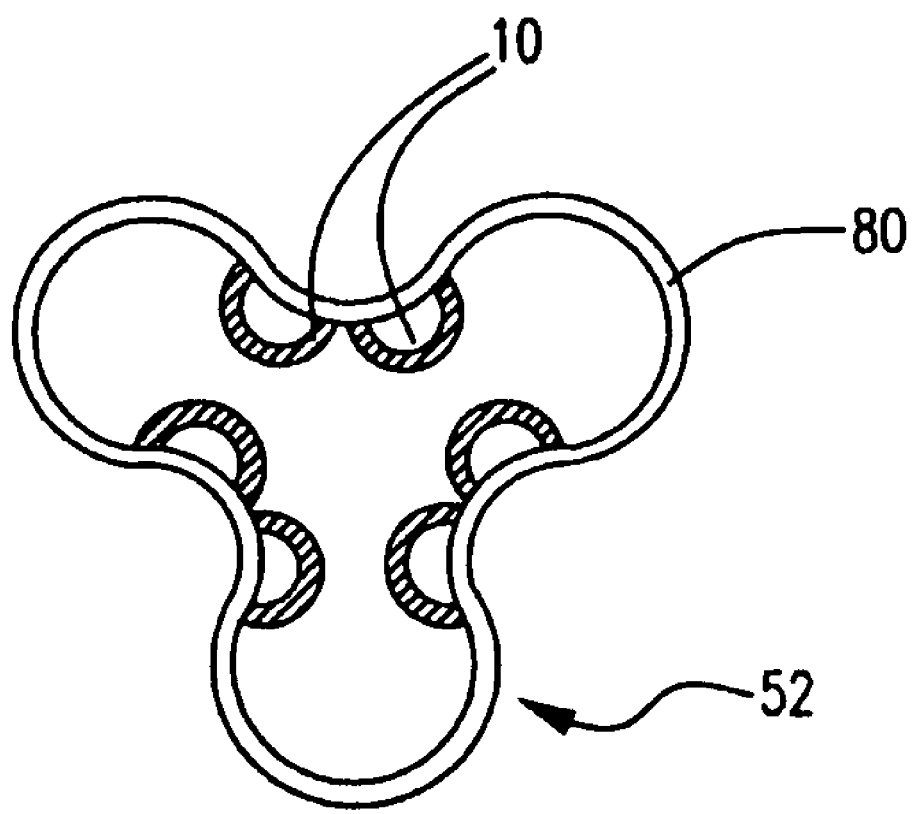
FIG. 28 is a radial cross-section of a balloon similar to that shown in FIGS. 26 and 27 after activation of the EAP active regions.

Upon contraction of the EAP active regions 10, the balloon 52 can be induced to fold or collapse on itself as shown in FIG. 28 resulting in the formation of wings 80. In this embodiment, three wings are shown. This is useful for withdrawal from a patient after use as described above.

Figure 29:
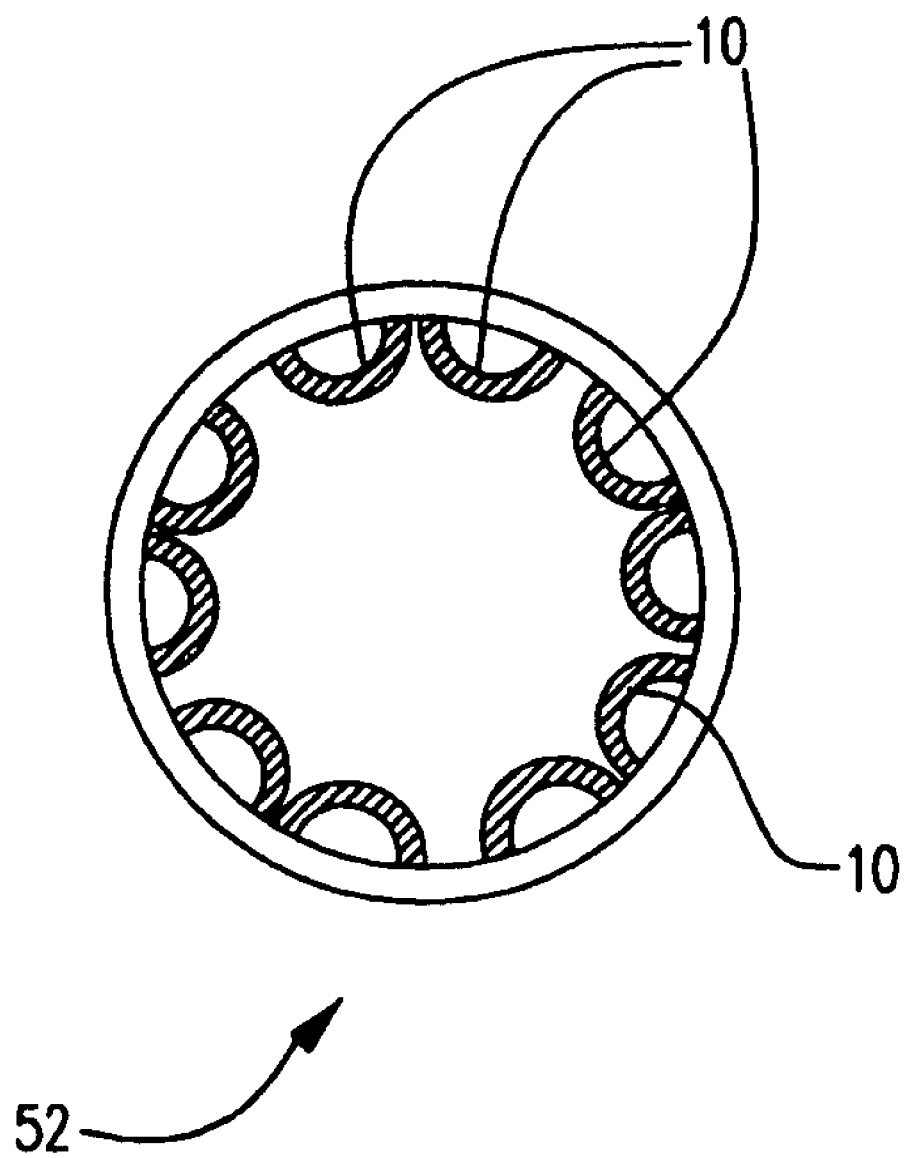
FIGS. 29 and 30 are radial cross-sections of a balloon similar to that shown in FIGS. 26-28 with a larger number of EAP active regions disposed on the inner surface of a balloon.
Figure 30:
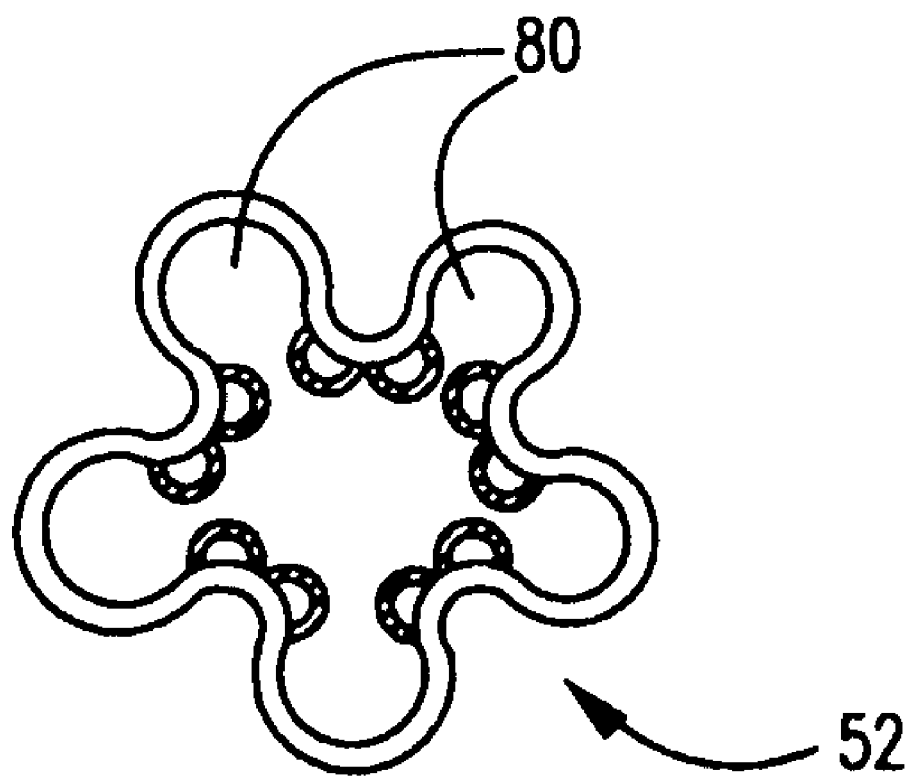

FIGS. 29 and 30 are radial cross-sections illustrating the use of EAP active regions 10 in the form of strips disposed on the inner surface of balloon 52 such that a five-wing structure is formed upon activation of the EAP active regions 10.

Figure 31:
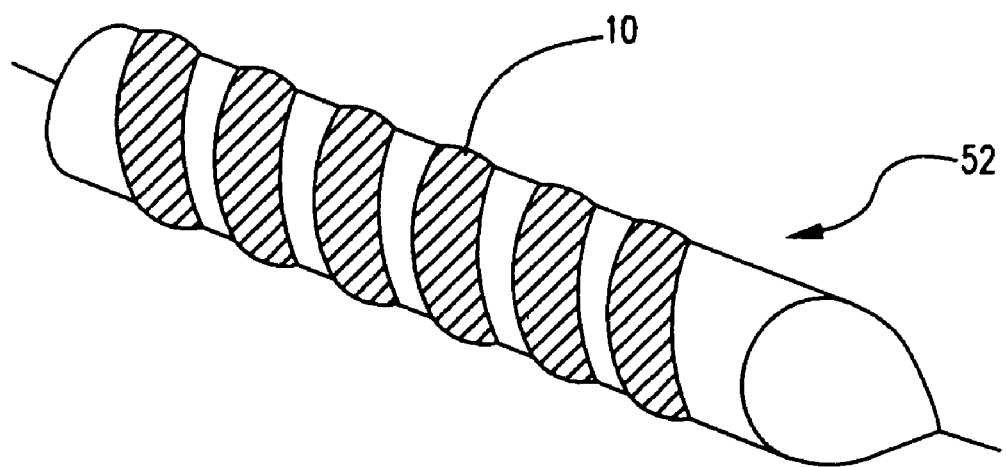
FIG. 31 is a perspective view of an expandable balloon member having a EAP active region spirally disposed about the balloon.

FIG. 31 is a perspective view of an expandable balloon member 52 having EAP active region 10 disposed in a spiral fashion about the balloon member 52 for controlled expansion and contraction of the balloon member. Rings disposed about the balloon at predetermined regular intervals rather than a spiral pattern, can also be used to incrementally control contraction/expansion of the balloon.

Balloon properties, such as compliance, can be varied or controlled using strategic positioning of EAP active regions, i.e. the balloon can be provided with lower and higher pressure segments that expand at different pressures to allow a physician to dilate different sized lesions without using multiple balloon catheters. For some medical procedures, it is desirable to do both a pre-dilatation and a post-dilatation of the stent which typically involves the use of two catheters: one with a balloon having a first smaller diameter and one with a balloon having a second larger diameter. Having one expandable member which can be dilated to different diameters can eliminate the need for using multiple catheters.

Figure 32:
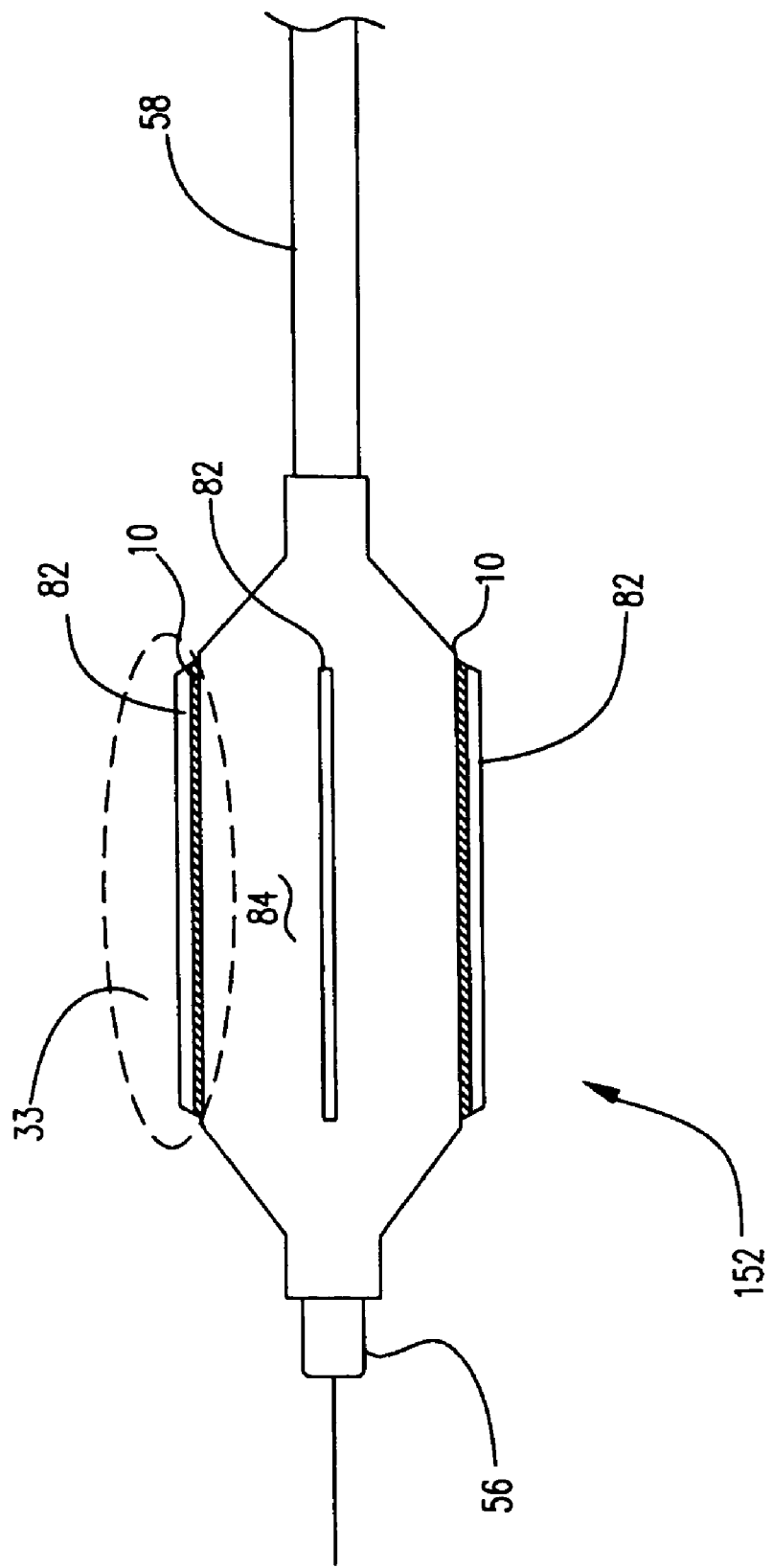
FIG. 32 is a side view of a cutting balloon having atherotomes mounted thereon.

EAP active regions may also be incorporated into balloon members which have blades or atherotomes attached thereto, i.e. cutting balloons. FIG. 32 is a side view of a balloon member 152 having atherotomes 82 disposed thereon. Disposed between balloon surface 84 and atherotome 82 is an EAP active region 10.

Figure 33A:
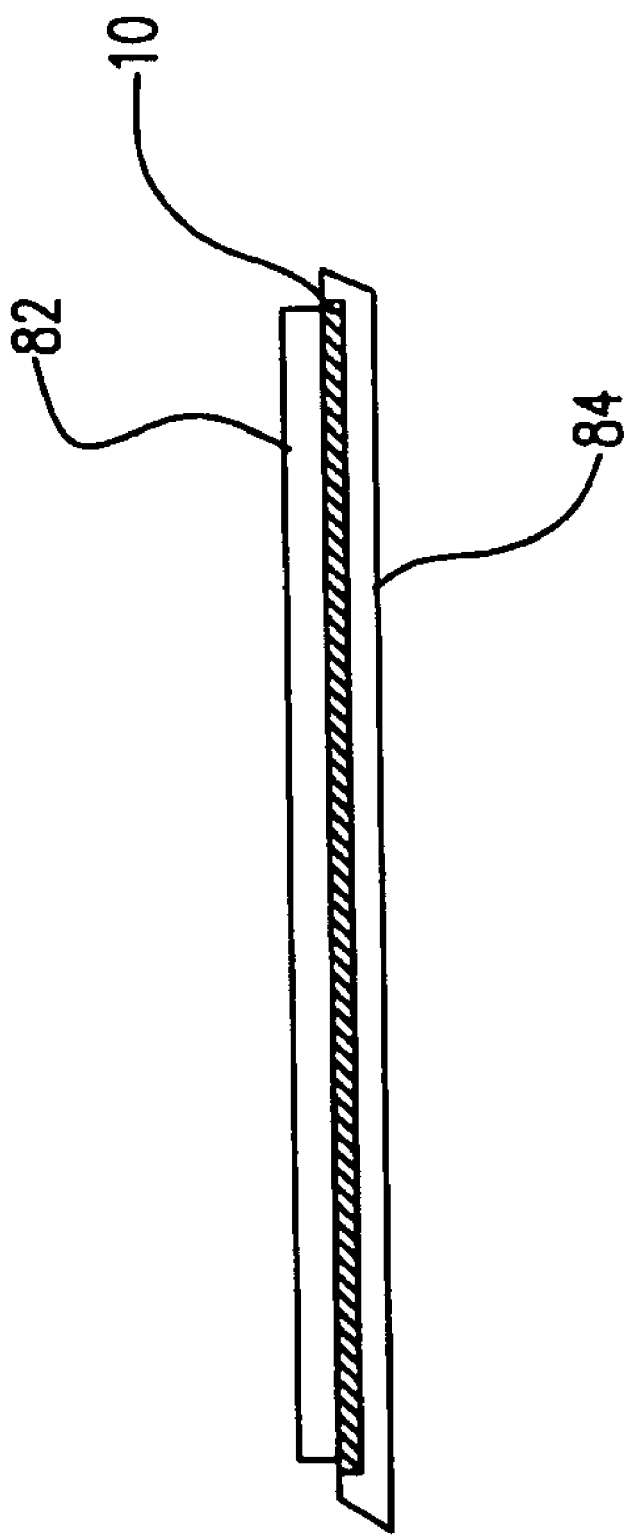
FIGS. 33A and 33B are partial exploded views taken at 31 in FIG. 30 before and after activation of EAP regions.
Figure 33B:
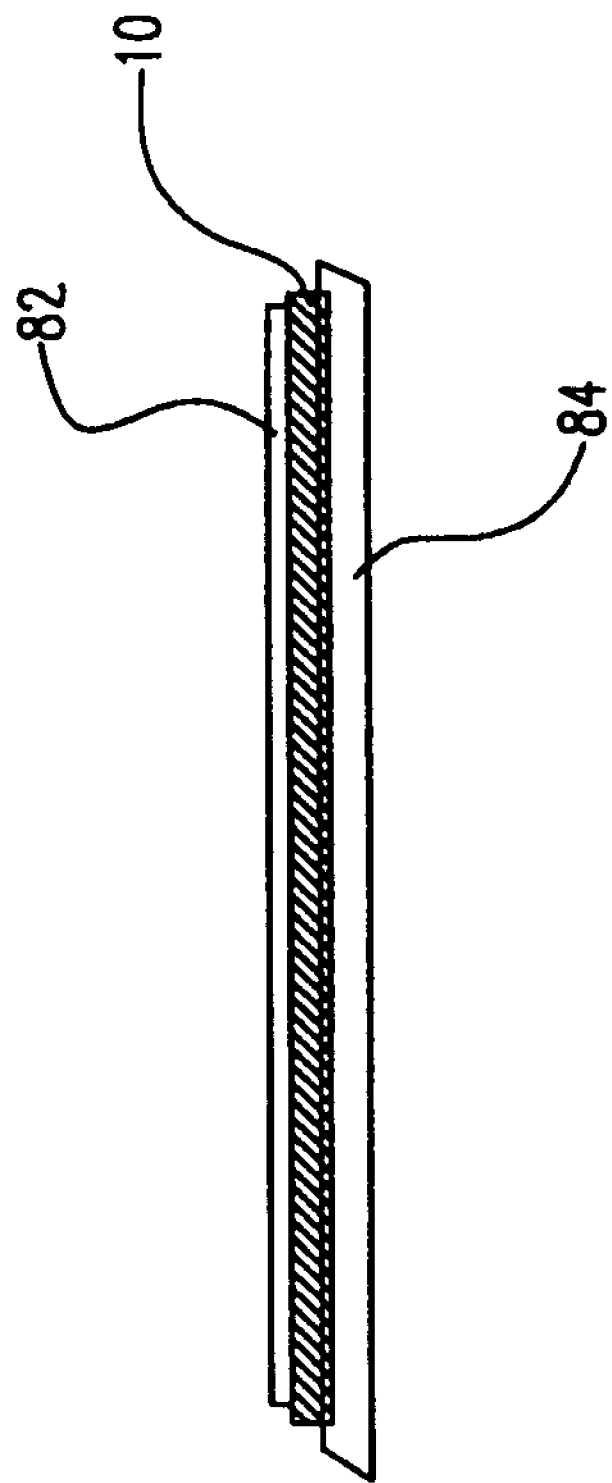

The EAP active regions 10 can be employed to control the movement of the atherotomes 82 including the angle of the blades and the distance that the atherotomes 82 extend outward at a perpendicular angle from the balloon surface. FIGS. 33A and 33B are exploded partial views taken at 33 in FIG. 30. FIG. 33A illustrates the EAP layer 10 disposed underneath atherotome 82, and is shown prior to expansion (activation) of the EAP active region 10. FIG. 33B is a partial exploded view of the EAP active 10 after expansion and shows atherotome 82 extending perpendicularly at a greater distance from balloon surface 84.

Figure 34A:
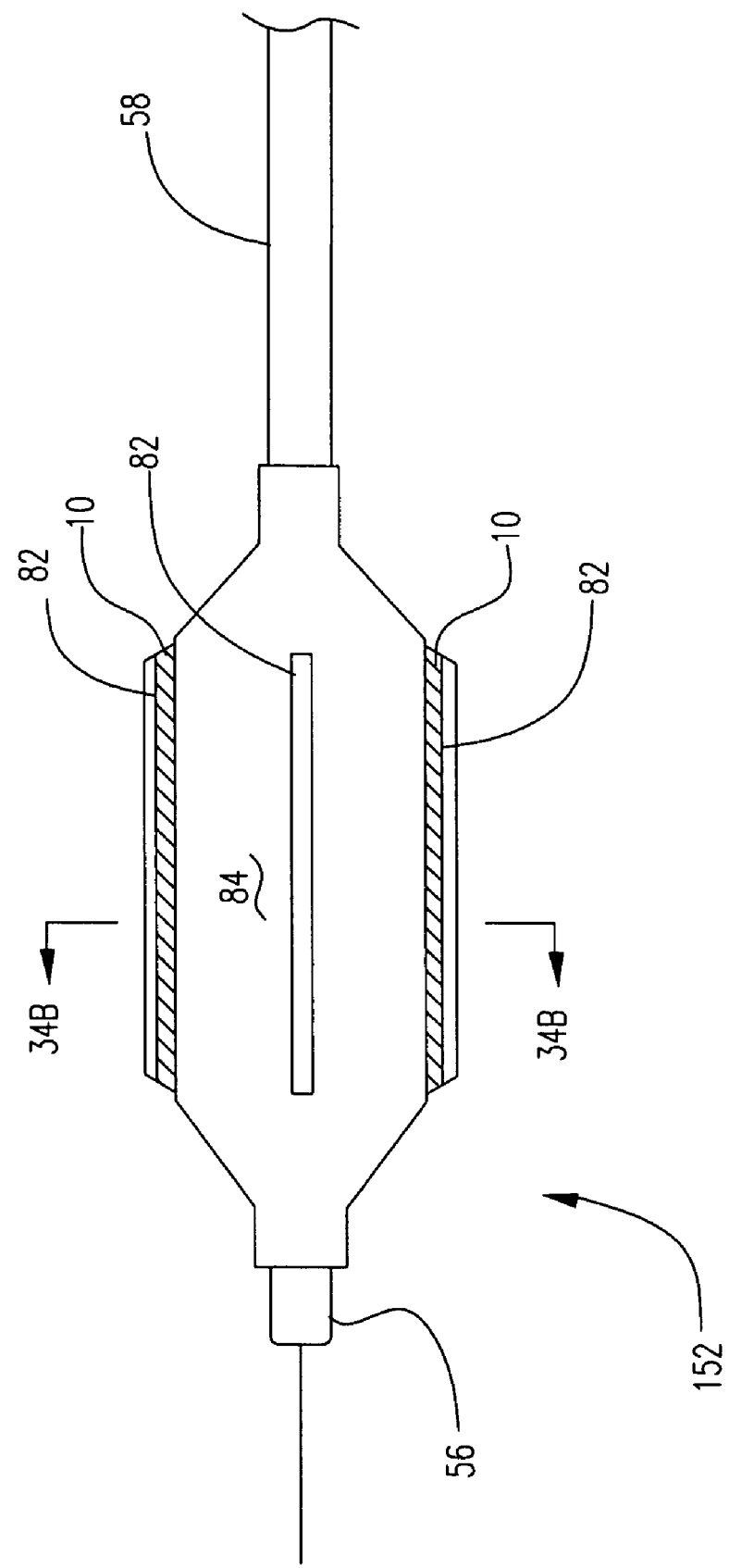
FIG. 34A is a side view of a cutting balloon having atherotomes mounted thereon.
Figure 34B:
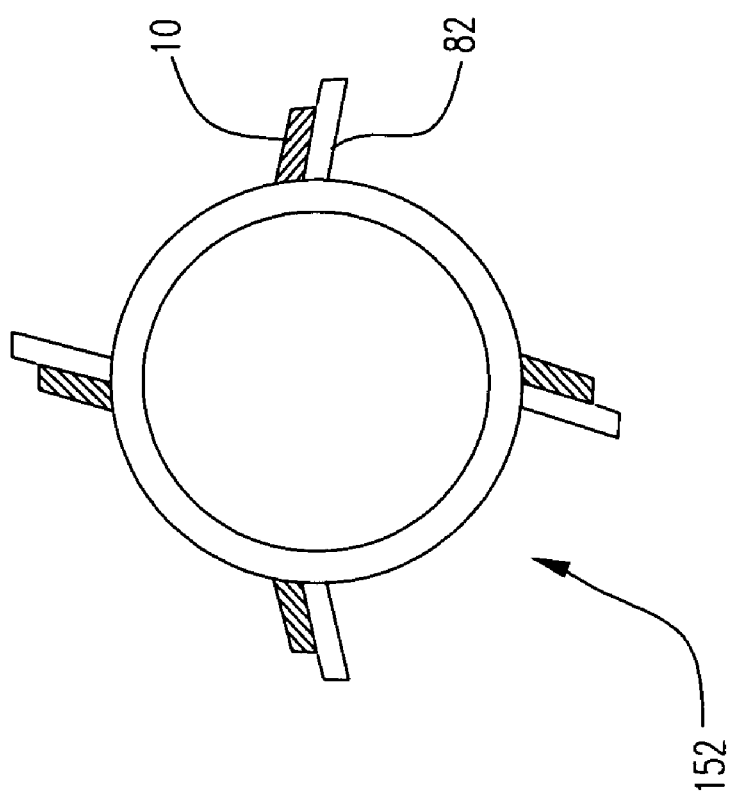
FIG. 34B is a radial cross-sectional view taken at section 34B-34B in FIG. 34A.

FIG. 34a is a side view of a cutting balloon 152 having atherotomes 82 mounted thereon. EAP active region 10 is shown disposed on the surface of blade 182 and can be activated to control the angle of the blade. The atherotomes are shown at an angle which is perpendicular to the surface 84 of balloon 152. FIG. 34b is a cross-sectional view taken at 34b-34b in FIG. 34a showing each blade 182 at a slight angle after activation of the EAP active region 10.

Figure 35:
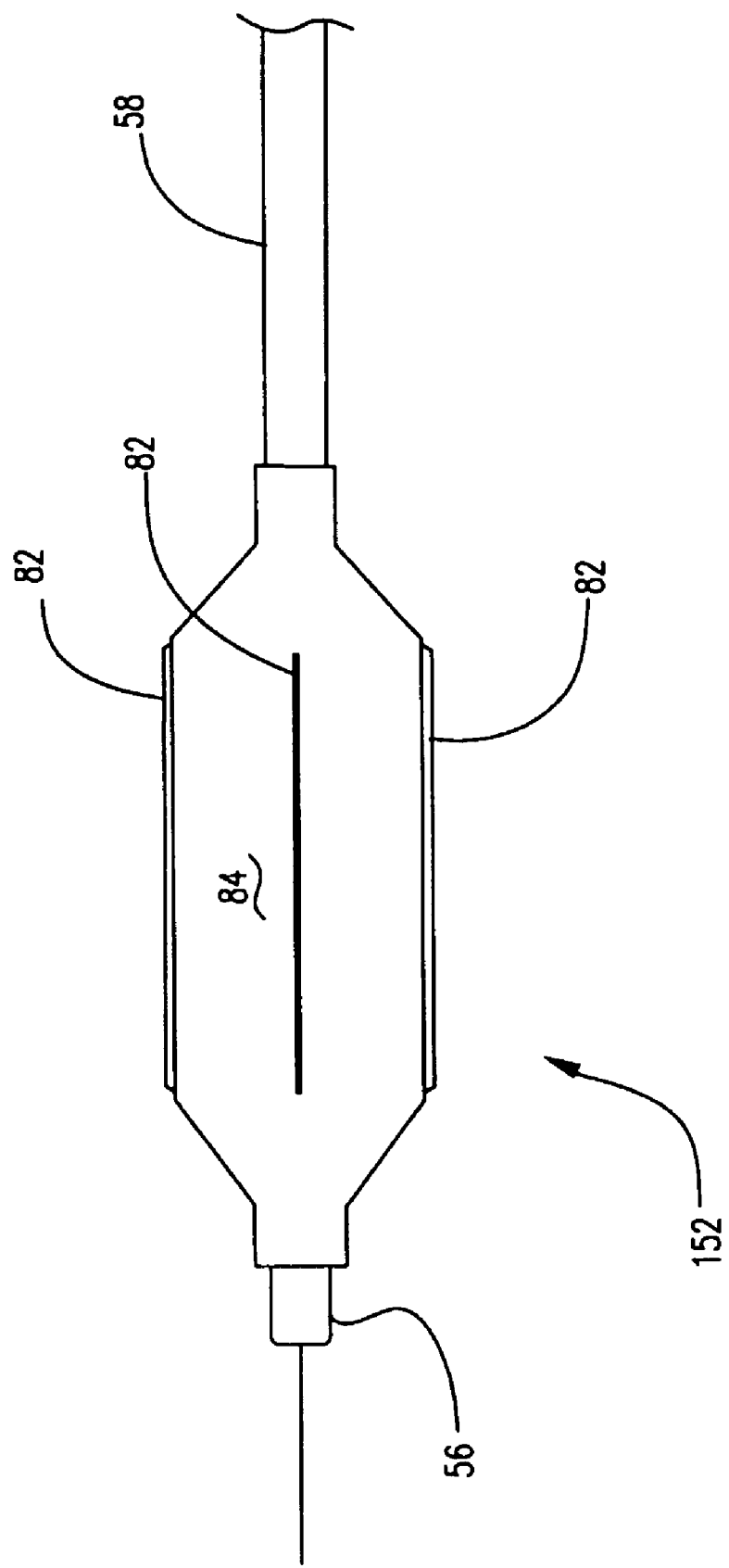
FIG. 35 is a side view of a cutting balloon similar to that shown in FIG. 32 after activation of EAP regions.

FIG. 35 is a side view of a cutting balloon 152 similar to that shown in FIG. 34 after activation of the EAP active regions. The atherotomes 82 are shown laying flat on the surface 84 of the balloon 152 after activation of the EAP active region 10 disposed on each atherotome 82.

Alternatively, rather than employing EAP active regions disposed on the balloon, the balloon or expandable member 102 for a catheter assembly itself may be constructed of EAP polymer.

Figure 36:
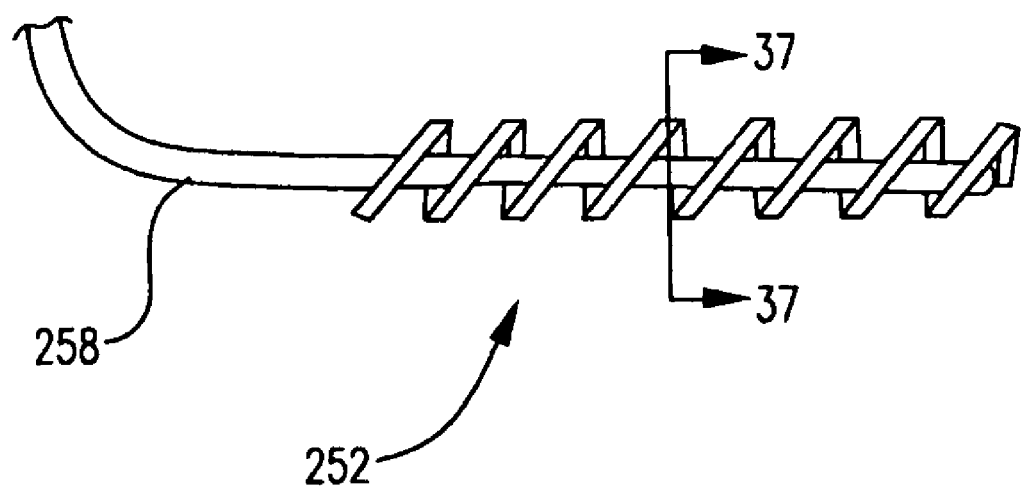
FIG. 36 is a perspective view of an expandable member for a catheter assembly which has been formed from EAP.

FIG. 36 illustrative an embodiment wherein an expandable EAP member 252 is disposed about the distal end of a catheter shaft 258. The EAP member may take on a coil-like spiral configuration. Upon activation, the EAP expands, increasing the overall diameter of the coiled structure. This can shorten the overall length of the coil for a desired effect. In an inactive state, the diameter of the coil can become smaller and the length of the coil increases. The expandable member illustrated in this embodiment may also be employed for delivery of medical devices, such as a stent. The stent may be disposed about the coil in its inactive state. Once actuated, the diameter of the expandable member increases so as to expand the stent. The EAP coil can then be deactuated to decrease the diameter and withdraw the coil from the stent.

Other similar alternative structure may include a series of bands, or several spirals which can be actuated/deactuated for a similar effect.

Figure 37:
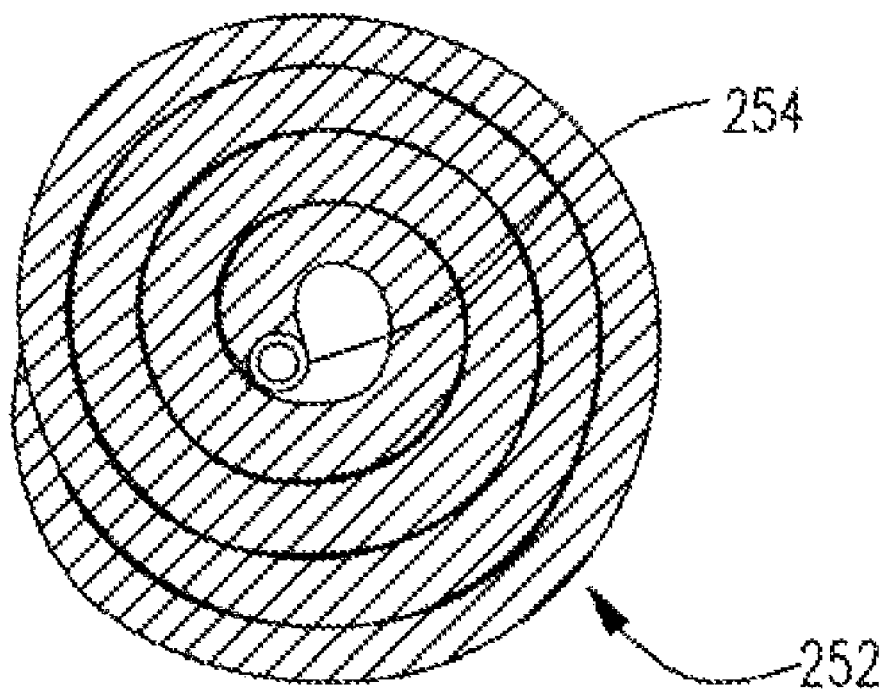
FIGS. 37-38 are radial cross-sections of the expandable member shown in FIG. 36 taken at section 37-37 in FIG. 36.

In another embodiment, an expandable member 252 is configured by employing EAP in a roll form as shown as a radial cross-section in FIG. 37. EAP in a sheet form is coiled about a longitudinal axis and forms a central lumen 254. This type of structure can be employed to replace a conventional expandable balloon member typically expanded through the use of inflation fluid. Upon actuation of expandable member 252, the volume of the roll increases thereby increasing in diameter.

Figure 38:
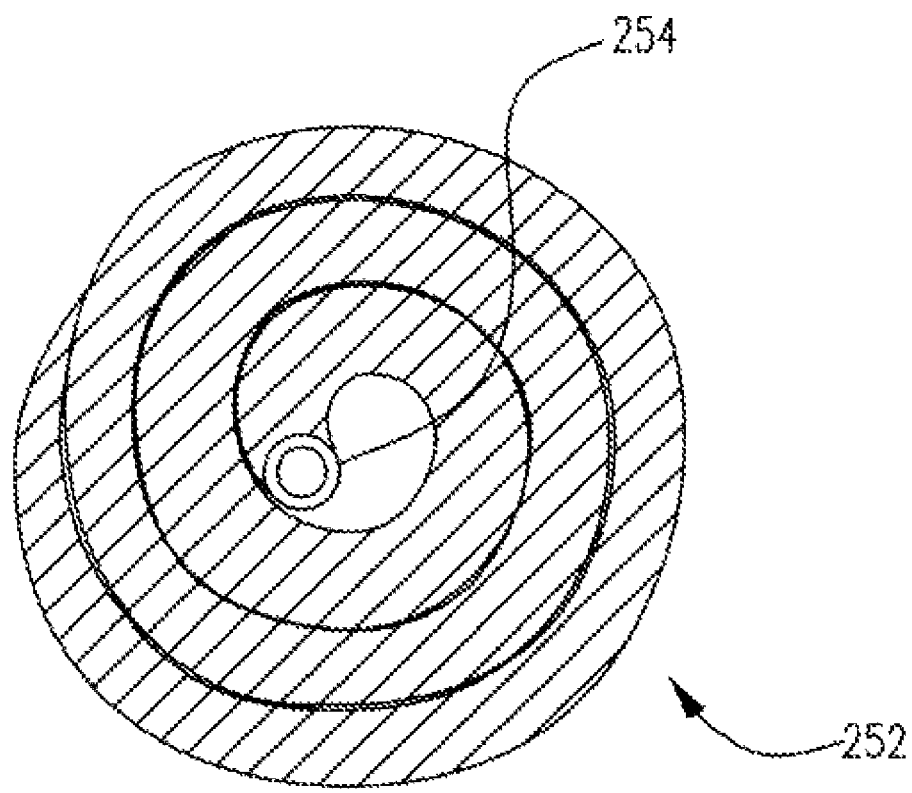

For stent delivery, a stent may be disposed about the expandable EAP member 252. Upon activation and expansion of the EAP member 252 as shown in radial cross-section in FIG. 38, the stent will also expand and can be deployed in a patient's vessel. Once deployed, the EAP member 252, may then be induced to contract for withdrawal from the vessel.

Figure 39A:
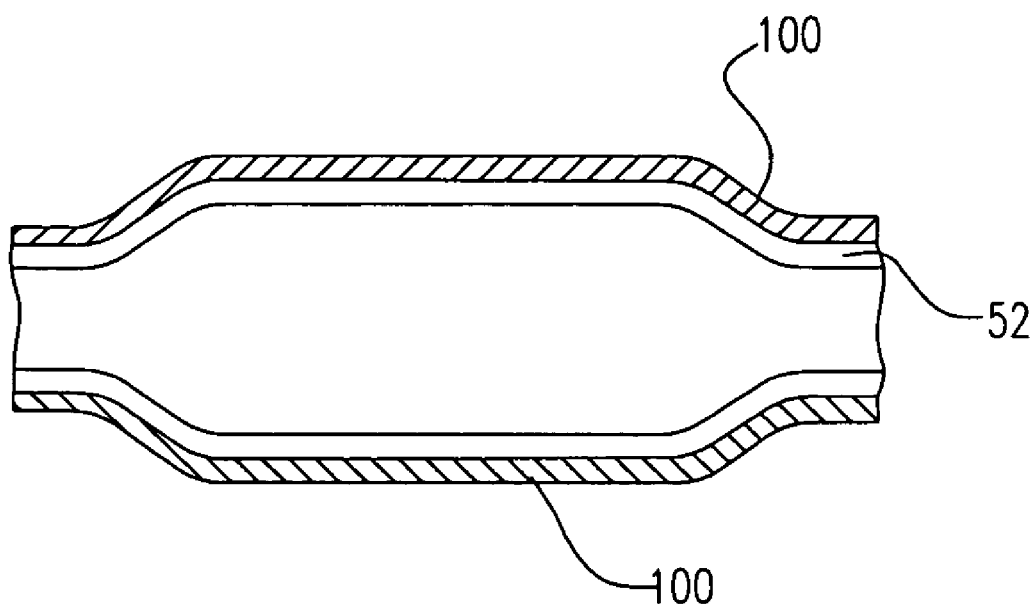
FIG. 39a is a longitudinal cross-section of a balloon having an EAP protective sheath.
Figure 39B:
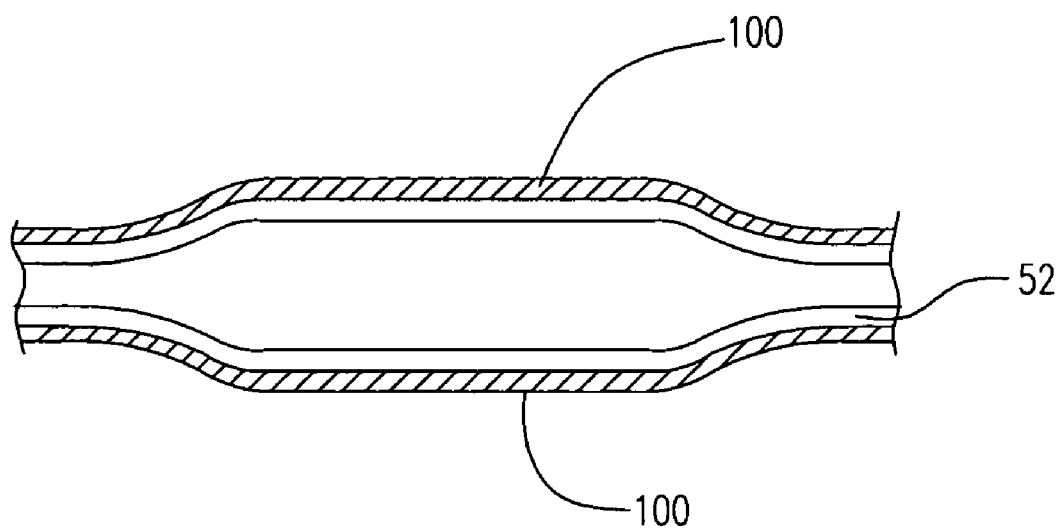
FIG. 39b is a longitudinal cross-section of a balloon similar to that shown in FIG. 39a after deactuation/contraction of the EAP protective sheath.
Figure 39C:
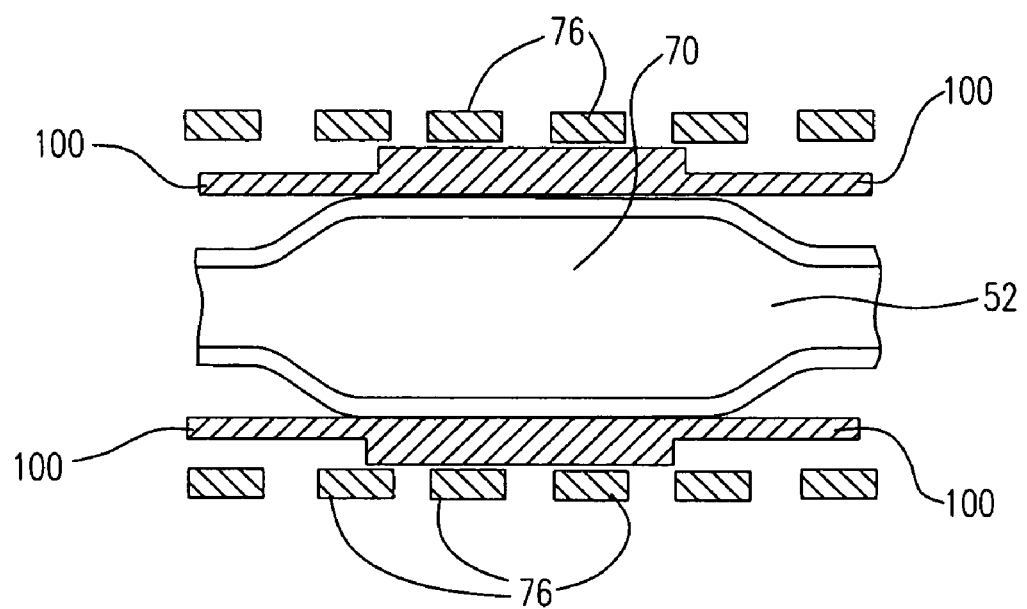
FIG. 39c is a longitudinal cross-section of an alternative configuration of an EAP sheath for center-up stent deployment.

In any of the embodiments described above, the balloon may further have a protective balloon cover which can be positioned over the balloon. The balloon cover is typically positioned over the balloon when the balloon is in its folded state. FIG. 39a is a longitudinal cross-section of a balloon 52 having a protective balloon cover 100 formed using EAP positioned thereon. The EAP cover 100 can be contracted following assembly to minimize the balloon profile and to hold the cover 100 in place as shown in FIG. 39b. Of course, the balloon may be in a folded configuration prior to disposing the cover 100 on the balloon as well. See for example, U.S. Pat. No. 6,991,639, the entire content of which is incorporated by reference herein (see specifically FIG. 49, which illustrates a protective cover on a folded balloon). The cover 100 is removed prior to delivery of the catheter during a medical procedure.

A stent may optionally be disposed over the sheath. In one embodiment, a stent 76 is disposed over EAP sheath 100 which is disposed over balloon 52, as shown in a longitudinal cross-sectional view in FIG. 36C. In this embodiment, sheath 100 is configured to have a thicker central portion which is positioned over balloon body 70. This alternative sheath configuration can aid in center-up balloon deployment.

The balloon in any of the embodiments described above may further advantageously include other coatings such as biocompatible coatings, lubricious coatings, coatings comprising therapeutic agents, etc. on the balloon surface as is known in the art.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. An expandable medical balloon, the balloon comprising a wall comprising body, waist and cone portions, at least one static state, at least one expanded state, and at least one deflated state, the expandable medical balloon comprising at least one active region, the at least one active region comprising electroactive polymer, the expandable medical balloon further comprising a folded state, the balloon having at least two folds in said folded state, each fold comprising said at least one active region.

2. The expandable medical balloon of claim 1 wherein the electroactive polymer is an electric electroactive polymer or an ionic electroactive polymer.

3. The expandable medical balloon of claim 2 wherein said electroactive polymer is an ionic electroactive polymer selected from the group consisting of conductive polymers, ionic polymer gels, ionomeric polymer-metal composites, carbon nanotubes and mixtures thereof.

4. The expandable medical balloon of claim 3 wherein said ionic electroactive polymer is a conductive polymer selected from the group consisting of polypyrroles, polyanilines, polythiophenes, polyethylenedioxythiophenes, poly(p-phenylene vinylene)s, polysulfones, polyacetylenes and mixtures thereof.

5. The expandable medical balloon of claim 1 further comprising waist, cones and body portions, at least one of said cones comprising the at least one active region.

6. The expandable medical balloon of claim 1 further comprising waist, cones and body portions, at least a portion of said body portion comprising the at least one active region.

7. The expandable medical balloon of claim 6 wherein said body portion comprises a plurality of said active regions, the balloon further comprising a longitudinal axis, the plurality of said active regions parallel the longitudinal axis.

8. The expandable medical balloon of claim 6 wherein said at least one active region is a circumferential band around said body portion.

9. The expandable medical balloon of claim 8 wherein said body portion comprises a plurality of said active regions, each active region forms a circumferential band around said body portion.

10. The expandable medical balloon of claim 9 wherein said plurality of said active regions are evenly spaced on said body portion.

11. The expandable medical balloon of claim 8 wherein the body portion further comprises a central region, and first and second end regions, the at least one active region is located at the central region of said body portion.

12. The expandable medical balloon of claim 8 wherein the body portion further comprises a central region, and first and second end regions, the at least one active region is located on at least one of said first region and said second end regions.

13. The expandable medical balloon of claim 1 wherein said balloon further comprises a longitudinal axis, the folds parallel to the longitudinal axis, and said active regions on said folds parallel the longitudinal axis.

14. The expandable medical balloon of claim 1, the folds further having a first side and a second side, each of said first side and said second side comprising at least one of said plurality of said active regions.

15. The expandable medical balloon of claim 1 further comprising waist, cones and body portions, the at least one active region in spiral fashion on at least the body portion.

16. The expandable medical balloon of claim 1 further comprising a sheath, the sheath further comprised of electro active polymer.

17. The expandable medical balloon of claim 1 wherein the distal end of said medical balloon is mounted on an inner catheter shaft, the inner catheter shaft comprising at least one second active region.

18. The expandable medical balloon of claim 1 further comprising a plurality of atherotomes.

19. The expandable medical balloon of claim 18 wherein said balloon comprises a plurality of said active regions, each of said plurality of atherotomes comprising at least one of said plurality of said active regions.

20. The expandable medical balloon of claim 18 wherein each of said plurality of atherotomes is comprised of electro active polymer.

* * * * *